United States Patent
Agoram et al.

(10) Patent No.: US 10,556,939 B2
(45) Date of Patent: Feb. 11, 2020

(54) GLUCAGON/GLP-1 AGONISTS FOR THE TREATMENT OF OBESITY

(71) Applicant: MedImmune Limited, Cambridge (GB)

(72) Inventors: Balaji Agoram, Gaithersburg, MD (US); Madeleine Antonsson, Mölndal (SE); Maria A. Bednarek, Cambridge (GB); Nicole Burmeister, Cambridge (GB); Lambertus Benthem, Cambridge (GB); David Fairman, Cambridge (GB); Maria Fritsch-Fredin, Mölndal (SE); Ronald Jackson, Cabridge (GB); Rasmus Jansson Lofmark, Cambridge (GB); Jacqueline Metcalfe, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 68 days.

(21) Appl. No.: 15/673,826

(22) Filed: Aug. 10, 2017

(65) Prior Publication Data

US 2017/0342121 A1 Nov. 30, 2017

Related U.S. Application Data

(62) Division of application No. 14/650,469, filed as application No. PCT/IB2013/003191 on Dec. 10, 2013, now Pat. No. 9,765,130.

(60) Provisional application No. 61/735,823, filed on Dec. 11, 2012.

(51) Int. Cl.
| | | |
|---|---|---|
| *A61K 38/26* | (2006.01) | |
| *C07K 14/605* | (2006.01) | |
| *A61K 38/00* | (2006.01) | |

(52) U.S. Cl.
CPC ............ *C07K 14/605* (2013.01); *A61K 38/00* (2013.01)

(58) Field of Classification Search
CPC .............................. C07K 14/605; A61K 38/26
See application file for complete search history.

(56) References Cited

FOREIGN PATENT DOCUMENTS

| EP | 0154316 | 9/1985 |
|---|---|---|
| EP | 0401384 A1 | 12/1990 |
| EP | 2173890 | 3/2011 |
| WO | WO 2004/022004 A2 | 3/2004 |
| WO | WO 2011/143209 A1 | 11/2010 |
| WO | WO 2010/148089 A1 | 12/2010 |

OTHER PUBLICATIONS

Perfetti et al., Eur. J. Endocr. 143, 717-725, 2000.*
Gutniak et al., New England J. Med. 30 326:1316-1322, 1992.*
Chae, S.Y., et al., "The fatty acid conjugated exendin-4 analogs for type 2 antidiabetic therapeutics", Journal of Controlled Release, Elsevier, Amsterdam, NL, 144, pp. 10-16, May 21, 2010.
International search report in PCT Application No. PCT/IB2013/003191, dated Jul. 31, 2014.
International Preliminary Report on Patentability in International Application No. PCT/IB2013/003191, dated Jun. 16, 2015.
Written Opinion for International Application No. PCT/IB2013/003191, dated Jun. 11, 2015.
Merrifield, R.B., et al., "Solid Phase Peptide Synthesis. I. The Synthesis of a Tetrapeptide," Journal of the American Chemical Society, vol. 85 (14), pp. 2149-2154, Jul. 1963.
Baggio, L.L., et al., "A Recombinant Human Glucagon-Like Peptide (GLP)-1-Albumin Proteing (Albugon) Mimics Peptidergic Activation of GLP-1 Receptor-Dependent Pathways Coupled with Satiety, Gastrointestinal Motility, and Glucose Homeostasis", Diabetes, vol. 53, pp. 2492-2500, Sep. 2004.
Barrington, P. et al., "LY2189265, a long-acting glucagon-like peptide-1 analogue, showed a dose-dependent effect on insulin secretion in healthy subjects," Diabetes, Obesity and Metabolism, 13, pp. 434-438, 2011.
Paulik, P., et al., Poster 1946, "Long-Acting PYY and GLP-1 Agonism in Combination Synergistically Normalizes Weight, Glucose, Metabolic and Metabolomic Parameters in Diet Induced Obese Mice," American Diabetes Association, 2012.
Schellenberger, V., et al., "A recombinant polypeptide extends the in vivo half-life of peptides and proteins in a tunable manner," Nature Biotechnology, 27, pp. 1186-1190, Nov. 15, 2009.
Dennis, M.S., et al., "Albumin Binding as a General Strategy for Improving the Pharmacokinetics of Proteins," The Journal of Biology Chemistry, vol. 277, No. 38, pp. 35035-35043, 2002.
Walker, A. et al., "Anti-serum albumin domain antibodies in the development of highly potent, efficacious and long-acting interferon," Protein Engineering, Design & Selection, vol. 23, No. 4, pp. 271-278, 2010.
Hjorth, S.A., et al., "Glucagon and Glucagon-Like Peptide 1: Selective Receptor Recognition via Distinct Peptide Epitopes", Journal of Biological Chemistry, American Society of Biochemistry and molecular Biology, US., vol. 269, No. 48, pp. 30121-30124, Jan. 1, 1994.
Karlin, S., et al., "Applications and statistics for multiple high-scorng segments in molecular sequences," Proc. Natl. Acad. Sci. USA, 90, 5873-5877, Jun. 1993.
Underwood, C.R., et al., "Crystal Structure of Glucagon-like Peptide-1 in Complex with the Extracellular Domain of the Glucagon-like Peptide-1 Receptor," The Journal of Biological Chemistry, vol. 285, No. 1, pp. 723-730, Jan. 1, 2010.
Runge, S., et al., "Crystal Structure of the Ligand-bound Glucagon-like Peptide-1 Receptor Extracellular Domain," The Journal of Biological Chemistry, vol. 283, No. 17, pp. 11340-11347, Apr. 25, 2008.
Francis, G.E., "Protein modification and fusion proteins," Focus on Growth Factors, 1992; 3:4-10, Mediscript.
Bregman, M.D., et al., "Evaluation of Modifications Leading to Antagonism and Agonism," The Journal of Biological Chemistry, vol. 255, No. 24, Issue of Dec. 25, 1980, pp. 11725-11731.

(Continued)

*Primary Examiner* — Gyan Chandra

(57) ABSTRACT

This disclosure provides GLP-1/glue agon agonist peptides for the treatment of metabolic diseases, e.g., obesity.

3 Claims, 8 Drawing Sheets

Specification includes a Sequence Listing.

(56) References Cited

OTHER PUBLICATIONS

Longo, E., et al., "The Effect of Palmitoylation on the conformation and physical stability of a peptide hormone," International Journal of Pharmaceutics, 472, 2014, pp. 156-164.

Database Geneseq [online], Jan. 5, 2012, Glucagon analog peptide sequence, SEQ ID 524, XP002726912, retrieved from EBI accession No. GSP:AZP67221.

* cited by examiner

SEQUENCE LISTING

```
<160> NUMBER OF SEQ ID NOS: 26

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
```

<210> SEQ ID NO 4
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (2)..(2)
<223> OTHER INFORMATION: Xaa is Gly or Ser
<220> FEATURE:
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (15)..(15)
<223> OTHER INFORMATION: Xaa is Asp or Glu
<220> FEATURE:
<221> NAME/KEY: MISC_FEATURE
<222> LOCATION: (16)..(16)
<223> OTHER INFORMATION: Xaa is Ser or Gly
<220> FEATURE:
<221> NAME/KEY: MISC_FEATURE
<222> LOCATION: (17)..(17)
<223> OTHER INFORMATION: Xaa is Glu, Arg, Gln, or Lys
<220> FEATURE:
<221> NAME/KEY: MISC_FEATURE
<222> LOCATION: (18)..(18)
<223> OTHER INFORMATION: Xaa is Arg, Ser, or Ala
<220> FEATURE:
<221> NAME/KEY: MISC_FEATURE
<222> LOCATION: (20)..(20)
<223> OTHER INFORMATION: Xaa is Arg, Lys, or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (23)..(23)
<223> OTHER INFORMATION: Xaa is Val or Ile
<220> FEATURE:
<221> NAME/KEY: MISC_FEATURE
<222> LOCATION: (24)..(24)
<223> OTHER INFORMATION: Xaa is Ala or Gln
<220> FEATURE:
<221> NAME/KEY: MISC_FEATURE
<222> LOCATION: (27)..(27)
<223> OTHER INFORMATION: Xaa is Glu or Val
<220> FEATURE:
<221> NAME/KEY: MISC_FEATURE
<222> LOCATION: (28)..(28)
<223> OTHER INFORMATION: Xaa is Ala or Lys
<220> FEATURE:
<221> NAME/KEY: MISC_FEATURE
<222> LOCATION: (30)..(30)
<223> OTHER INFORMATION: Xaa is Gly or Arg

<400> SEQUENCE: 4

His Xaa Gln Gly Thr Phe Thr Ser Asp Xaa Ser Xaa Xaa Leu Xaa Xaa
 1               5                  10                  15

Xaa Xaa Ala Xaa Xaa Phe Xaa Xaa Trp Leu Xaa Xaa Gly Xaa
            20                  25                  30

```
<210> SEQ ID NO 5
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (17)..(17)
<223> OTHER INFORMATION: Xaa is Glu, Arg, Gln, or Lys
<220> FEATURE:
<221> NAME/KEY: MISC_FEATURE
<222> LOCATION: (18)..(18)
<223> OTHER INFORMATION: Xaa is Arg, Ser, or Ala
<220> FEATURE:
<221> NAME/KEY: MISC_FEATURE
<222> LOCATION: (27)..(27)
<223> OTHER INFORMATION: Xaa is Glu or Val

<400> SEQUENCE: 5

His Ser Gln Gly Thr Phe Thr Ser Asp Xaa Ser Xaa Xaa Leu Asp Ser
1               5                   10                  15

Xaa Xaa Ala Arg Asp Phe Val Ala Trp Leu Xaa Ala Gly Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (27)..(27)
<223> OTHER INFORMATION: Xaa is Glu or Val

<400> SEQUENCE: 6

His Ser Gln Gly Thr Phe Thr Ser Asp Xaa Ser Xaa Xaa Leu Asp Ser
1               5                   10                  15

Glu Arg Ala Arg Asp Phe Val Ala Trp Leu Xaa Ala Gly Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
```

```
<221> NAME/KEY: MISC_FEATURE
<222> LOCATION: (10)..(10)
<223> OTHER INFORMATION: Xaa is Tyr or Lys
<220> FEATURE:
<221> NAME/KEY: MISC_FEATURE
<222> LOCATION: (12)..(12)
<223> OTHER INFORMATION: Xaa is Lys, Glu, Arg, or Ser
<220> FEATURE:
<221> NAME/KEY: MISC_FEATURE
<222> LOCATION: (13)..(13)
<223> OTHER INFORMATION: Xaa is Lys or Tyr
<220> FEATURE:
<221> NAME/KEY: MISC_FEATURE
<222> LOCATION: (27)..(27)
<223> OTHER INFORMATION: Xaa is Glu or Val

<400> SEQUENCE: 7

His Ser Gln Gly Thr Phe Thr Ser Asp Xaa Ser Xaa Xaa Leu Asp Ser
1               5                   10                  15

Arg Ser Ala Arg Asp Phe Val Ala Trp Leu Xaa Ala Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 8

His Ser Gln Gly Thr Phe Thr Ser Asp Tyr Ser Lys Lys Leu Asp Ser
1               5                   10                  15

Glu Arg Ala Arg Asp Phe Val Ala Trp Leu Val Ala Gly Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 9

His Ser Gln Gly Thr Phe Thr Ser Asp Tyr Ser Lys Lys Leu Asp Ser
1               5                   10                  15

Arg Ser Ala Arg Asp Phe Val Ala Trp Leu Val Ala Gly Gly
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (12)..(12)
<223> OTHER INFORMATION: Xaa is Lys, Glu, or Arg

<400> SEQUENCE: 10

His Ser Gln Gly Thr Phe Thr Ser Asp Lys Ser Xaa Tyr Leu Asp Ser
1               5                   10                  15

Glu Arg Ala Arg Asp Phe Val Ala Trp Leu Glu Ala Gly Gly
            20                  25                  30

<210> SEQ ID NO 11
<211> LENGTH: 30
```

```
<212> TYPE: PRT
<213> ORGANISM: Artificial Sequence
<220> FEATURE:
<223> OTHER INFORMATION: chimeric GLP-1/glucagon peptide
<220> FEATURE:
<221> NAME/KEY: MISC_FEATURE
<222> LOCATION: (12)..(12)
<223> OTHER INFORMATION: Xaa is Lys, Glu, Arg, or Ser

<400> SEQUENCE: 11

His Ser Gln Gly Thr Phe Thr Ser Asp Lys Ser Xaa Tyr Leu Asp Ser
1               5                   10                  15

Arg Ser Ala Arg Asp Phe Val Ala Trp Leu Glu Ala Gly Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 12

His Ser Gln Gly Thr Phe Thr Ser Asp Lys Ser Glu Tyr Leu Asp Ser
1               5                   10                  15

Glu Arg Ala Arg Asp Phe Val Ala Trp Leu Glu Ala Gly Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 13

His Ser Gln Gly Thr Phe Thr Ser Asp Lys Ser Glu Tyr Leu Asp Ser
1               5                   10                  15

Arg Ser Ala Arg Asp Phe Val Ala Trp Leu Glu Ala Gly Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 14

His Ser Gln Gly Thr Phe Thr Ser Asp Lys Ser Arg Tyr Leu Asp Ser
1               5                   10                  15

Glu Arg Ala Arg Asp Phe Val Ala Trp Leu Glu Ala Gly Gly
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 15

His Ser Gln Gly Thr Phe Thr Ser Asp Lys Ser Arg Tyr Leu Asp Ser
1               5                   10                  15

Arg Ser Ala Arg Asp Phe Val Ala Trp Leu Glu Ala Gly Gly
```

20                  25                  30

<210> SEQ ID NO 16
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 16

His Ser Gln Gly Thr Phe Thr Ser Asp Tyr Ser Lys Lys Leu Asp Ser
1               5                   10                  15

Glu Arg Ala Arg Asp Phe Val Ala Trp Leu Val Ala Gly Gly
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 17

His Ser Gln Gly Thr Phe Thr Ser Asp Lys Ser Glu Tyr Leu Asp Ser
1               5                   10                  15

Glu Arg Ala Arg Asp Phe Val Ala Trp Leu Glu Ala Gly Gly
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 18

His Ser Gln Gly Thr Phe Thr Ser Asp Lys Ser Arg Tyr Leu Asp Ser
1               5                   10                  15

Arg Ser Ala Arg Asp Phe Val Ala Trp Leu Glu Ala Gly Gly
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 19

His Ser Gln Gly Thr Phe Thr Ser Asp Lys Ser Glu Tyr Leu Asp Ser
1               5                   10                  15

Glu Arg Ala Arg Asp Phe Val Ala Trp Leu Glu Ala Gly Gly
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 20

His Ser Gln Gly Thr Phe Thr Ser Asp Lys Ser Ser Tyr Leu Asp Ser
1               5                   10                  15

Arg Ser Ala Arg Asp Phe Val Ala Trp Leu Glu Ala Gly Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 21

His Ser Gln Gly Thr Phe Thr Ser Asp Lys Ser Ser Tyr Leu Asp Ser
1               5                   10                  15

Arg Arg Ala Arg Asp Phe Val Ala Trp Leu Glu Ala Gly Gly
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 22

His Ser Gln Gly Thr Phe Thr Ser Asp Lys Ser Lys Tyr Leu Glu Gly
1               5                   10                  15

Gln Ala Ala Lys Glu Phe Ile Ala Trp Leu Glu Lys Gly Arg
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: chimeric GLP-1/glucagon peptide

<400> SEQUENCE: 23

His Gly Gln Gly Thr Phe Thr Ser Asp Tyr Ser Lys Tyr Leu Asp Ser
1               5                   10                  15

Lys Arg Ala Gln Asp Phe Val Gln Trp Leu Val Ala Gly Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: G931
<220> FEATURE:
<221> NAME/KEY: MISC_FEATURE
<222> LOCATION: (13)..(13)
<223> OTHER INFORMATION: Xaa is K(gE-palm)

<400> SEQUENCE: 24

His Ser Gln Gly Thr Phe Thr Ser Asp Tyr Ser Lys Xaa Leu Asp Ser
1               5                   10                  15

Glu Arg Ala Arg Asp Phe Val Ala Trp Leu Val Ala Gly Gly
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: G934
<220> FEATURE:

```
<221> NAME/KEY: MISC_FEATURE
<222> LOCATION: (10)..(10)
<223> OTHER INFORMATION: Xaa is K(gE-palm)

<400> SEQUENCE: 25

His Ser Gln Gly Thr Phe Thr Ser Asp Xaa Ser Lys Tyr Leu Glu Gly
1               5                   10                  15

Gln Ala Ala Lys Glu Phe Ile Ala Trp Leu Glu Lys Gly Arg
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: G973
<220> FEATURE:
<221> NAME/KEY: MISC_FEATURE
<222> LOCATION: (10)..(10)
<223> OTHER INFORMATION: Xaa is K(gE-palm)

<400> SEQUENCE: 26

His Ser Gln Gly Thr Phe Thr Ser Asp Xaa Ser Ser Tyr Leu Asp Ser
1               5                   10                  15

Arg Ser Ala Arg Asp Phe Val Ala Trp Leu Glu Ala Gly Gly
            20                  25                  30
```

GLUCAGON/GLP-1 AGONISTS FOR THE TREATMENT OF OBESITY

CROSS-REFERENCE TO RELATED APPLICATIONS

This application is a divisional application of U.S. application Ser. No. 14/650,469, filed on Jun. 8, 2015; said U.S. application Ser. No. 14/650,469 is a U.S. National Stage application of International Application No. PCT/M2013/003191, filed on Dec. 10, 2013, said International Application No. PCT/M2013/003191 claims benefit under 35 U.S.C. § 119(e) of the U.S. Provisional Application No. 61/735,823, filed Dec. 11, 2012. Each of the above listed applications is incorporated by reference herein in its entirety for all purposes.

REFERENCE TO SEQUENCE LISTING SUBMITTED ELECTRONICALLY

The content of the electronically submitted sequence listing in ASCII text file (Name: sequencelisting_ascii.txt; Size: 12.3 kilobytes; and Date of Creation: Dec. 10, 2013) filed with the application is incorporated herein by reference in its entirety.

BACKGROUND

Obesity is a major and growing health problem worldwide, and is associated with many life-threatening diseases such as cardiovascular disease, renal disease, hypertension, stroke, infertility, respiratory dysfunction, and type 2 diabetes.

Glucagon and glucagon-like peptide-1 (GLP-1) derive from pre-proglucagon, a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of proglucagon (53 to 81 of preproglucagon), while GLP-1 is produced as a 37-amino acid peptide that corresponds to amino acids 72 through 108 of proglucagon (92 to 128 of preproglucagon). GLP-1(7-36) amide or GLP-1(7-37) acid are biologically active forms of GLP-1, that demonstrate essentially equivalent activity at the GLP-1 receptor.

Glucagon is produced by the pancreas and interacts with the glucagon receptor ("glucR"). Glucagon acts in the liver to raise blood glucose via gluconeogenesis and glycogenolysis. When blood glucose begins to fall, glucagon signals the liver to break down glycogen and release glucose, causing blood glucose levels to rise toward a normal level.

GLP-1 has different biological activities compared to glucagon. It is secreted from gut L cells and binds to the GLP-1 receptor. Its activities include stimulation of insulin synthesis and secretion, inhibition of glucagon secretion, and inhibition of food intake.

Both glucagon and GLP-1, acting as agonists at their respective receptors, have been shown to be effective in weight loss. Certain GLP-1 analogs are being sold or are in development for treatment of obesity including, e.g., Liraglutide (VICTOZA® from Novo Nordisk) and Exenatide (Byetta® from Eli Lilly/Amylin).

There remains a need for more agents for effective treatment of obesity, for example, GLP-1/Glucagon agonist peptides with improved solubility, formulatability, stability, and efficacy.

BRIEF SUMMARY

This disclosure provides an isolated peptide comprising or consisting of the amino acid sequence:

HX2QGTFTSDX10SX12X13LX15X16X17X18AX20X21FX23X24WLX27X28GX30;

where X2 is G or S, X10 is Y or K, X12 is K, E, R, or S, X13 is K or Y, X15 is D or E. X16 is S or G, X17 is E, R, Q, or K, X18 is R, S, or A, X20 is R, K, or Q, X21 is D or E, X23 is V or I, X24 is A or Q, X27 is E or V, X28 is A or K, and X30 is G or R (SEQ ID NO:4). In certain aspects, X2 is S, X15 is D, X16 is S, X20 is R, X21 is D, X23 is V, X24 is A, X28 is A, and X30 is G (SEQ ID NO:5). In certain aspects, if X17 is E, then X18 is R, and if X17 is R, then X18 is S (SEQ ID NOs:6 and 7). In certain aspects, X10 is Y, X12 is K, X13 is K, and X27 is V (SEQ ID NOs:8 and 9). In certain aspects, X10 is K, X13 is Y, and X27 is E (SEQ ID NOs:10 and 11). In certain aspects, X12 is E (SEQ ID NOs:12 and 13), alternatively, X12 is R (SEQ ID NOs:14 and 15). In certain aspects, the isolated peptide comprises, or consists of SEQ ID NO:16. In certain aspects, the isolated peptide comprises, or consists of the amino acid sequence SEQ ID NOs: 17 or the amino acid sequence SEQ ID NO:19. In certain aspects, the isolated peptide comprises, or consists of SEQ ID NO:18.

In certain embodiments of the peptides described above, the carboxyl group of X30 is amidated. In other embodiments the carboxyl group is the unmodified acid.

Any of the peptides provided herein can further comprise one or more modified amino acids, for example, the addition of an acyl moiety, for example, the modification can be the addition of a palmitoyl moiety on the N(epsilon) group of a lysine residue. In certain embodiments, the palmitoyl group is linked to the lysine residue through a gamma glutamate linker. Alternative linkers have been used including beta alanine and aminohexanoic acid. Further alternative linkers are possible including linkers containing short PEG moieties for instance containing 2 or 4 PEG units.

In various embodiments, the isolated peptides provided herein can bind to a glucagon receptor, to a GLP-1 receptor, or to both a glucagon and a GLP-1 receptor. In certain aspects the glucagon receptor is a human glucagon receptor, and or the GLP-1 receptor is a human GLP-1 receptor. In certain aspects an isolated peptide as provided herein binds to a human glucagon receptor with an EC50 in the cAMP assay 1 (as described herein) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain aspects an isolated peptide as provided herein binds to a human GLP-1 receptor with an EC50 in the cAMP assay 1 of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain aspects, an isolated peptide as provided herein is an agonist of GLP-1 activity, an agonist of glucagon activity, or an agonist of both GLP-1 and glucagon activity. In some embodiments, an isolated peptide as provided herein binds to both a glucagon receptor and a GLP-1 receptor, and exhibits at least about 2-fold greater activity relative to the natural ligand at the GLP-1 receptor than at the glucagon receptor. In one embodiment the peptide has a 5 to 10 fold higher relative potency at the GLP1R, compared to GLP1, than at the glucagon receptor, relative to glucagon.

In certain aspects, an isolated peptide as provided herein can further comprise a heterologous moiety associated with the peptide. In some aspects, the heterologous moiety is a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, or any combination of two or more of such moieties.

Also provided is a pharmaceutical composition comprising an isolated peptide as described herein, and a carrier. Further provided is a kit including such a pharmaceutical composition.

Also provided is a method for treating or preventing a disease or condition caused or characterized by excess body weight, where the method includes administering to a subject in need of treatment an effective amount of an isolated peptide as provided herein, or a composition which includes such a peptide. In certain aspects, the disease or condition can be obesity, insulin resistance, glucose intolerance, pre-diabetes, increased fasting glucose, type 2 diabetes, hypertension, dyslipidemia (or a combination of these metabolic risk factors), glucagonomas, cardiovascular disease, e.g., congestive heart failure, atherosclerois, arteriosclerosis, coronary heart disease, or peripheral artery disease; stroke, respiratory dysfunction, renal disease, and any combination thereof. According to the method, an isolated peptide as described herein can be administered by injection, e.g., subcutaneous injection. According to the method, the peptide can be administered once per day. In certain embodiments, the subject is a human.

Also provided is a method for treating or preventing a disease or condition caused or characterized by excess body weight, where the method includes administering to a subject in need of treatment an effective amount of an isolated peptide as provided herein, or a composition which includes such a peptide. According to the method, an isolated peptide as described herein can be administered by injection, e.g., subcutaneous injection. According to the method, the peptide can be administered once per day. In certain embodiments, the subject is a human.

BRIEF DESCRIPTION OF THE DRAWINGS/FIGURES

FIG. 1 shows the mean percent of change in body weight from day zero in DIO mice following administration of glucagon/GLP-1 co-agonist peptide G730 at three different doses, compared to vehicle treatment, and treatment with Liraglutide. Starting body weight in the different groups were vehicle: 47.4±3.7 g, G730 10 nmol/kg: 44.5±2.2 g, G730 20 nmol/kg: 45.9±3.6 g and G730 50 nmol/kg: 46.1±2.4 g, respectively.

FIG. 2 shows the mean percent of change in body weight from day zero in DIO mice following administration of glucagon/GLP-1 co-agonist peptide G797 at three different doses, compared to vehicle treatment, and treatment with Liraglutide. Starting body weight in the different groups were vehicle: 47.4±3.7 g, G797 5 nmol/kg: 47.5±1.2 g, G797 20 nmol/kg: 47.4±2.2 g and G797 50 nmol/kg: 47.2±1.8 g, respectively.

DETAILED DESCRIPTION

Definitions

Figure 1:
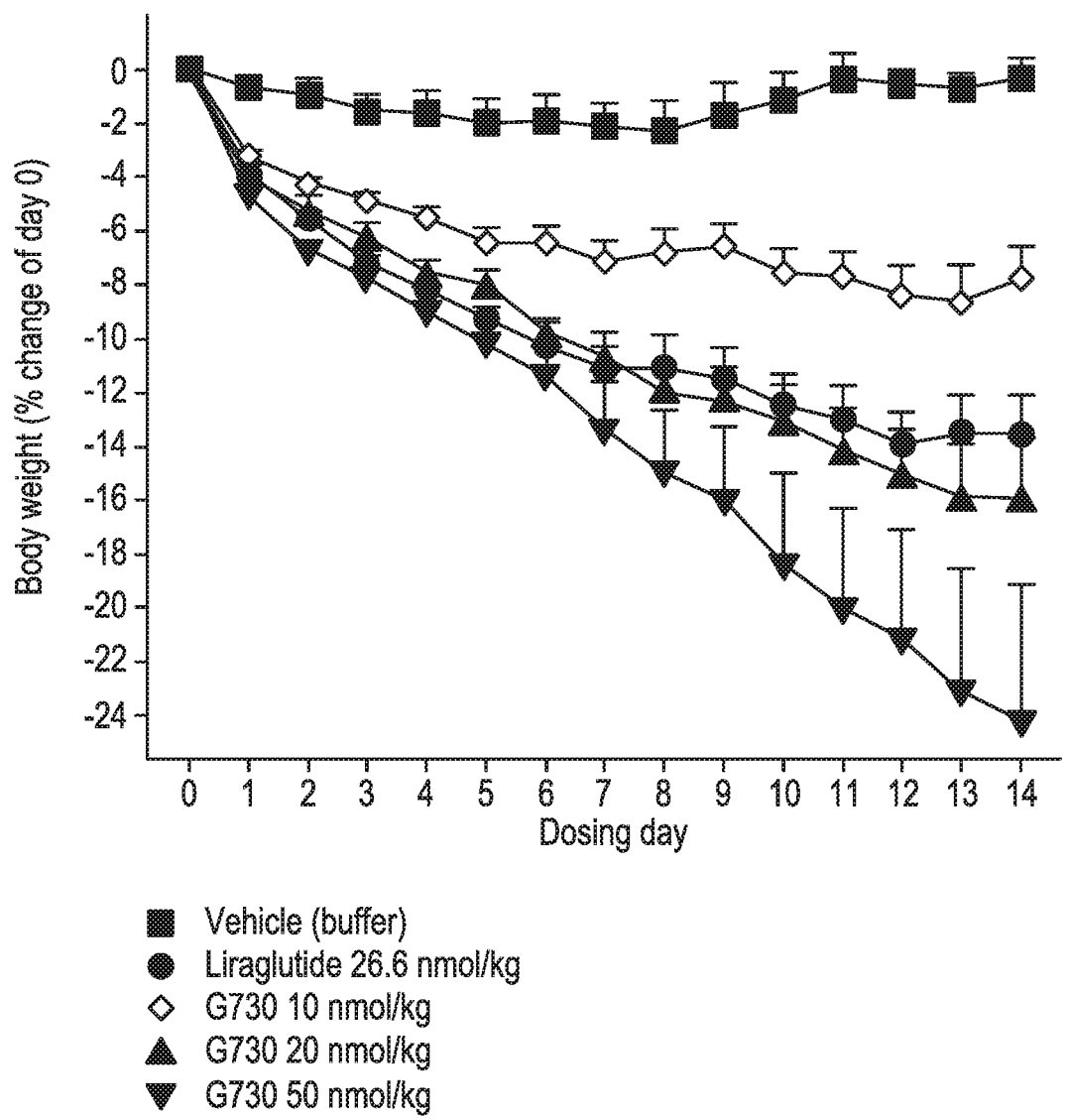

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and comprises any chain or chains of two or more amino acids. Thus, as used herein, a "peptide," a "peptide subunit," a "protein," an "amino acid chain," an "amino acid sequence," or any other term used to refer to a chain or chains of two or more amino acids, are included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, glycosylation, acetylation, phosphorylation, amidation, derivatization by known protecting/blocking groups, proteolytic cleavage, or modification by non-naturally occurring amino acids.

More specifically, the term "peptide" as used herein encompasses a full length peptides and fragments, variants or derivatives thereof, e.g., a GLP-1/glucagon agonist peptide (e.g., 29, 30, or 31 amino acids in length). A "peptide" as disclosed herein, e.g., a GLP-1/glucagon agonist peptide, can be part of a fusion polypeptide comprising additional components such as, e.g., an Fc domain or an albumin domain, to increase half-life. A peptide as described herein can also be derivatized in a number of different ways.

The terms "fragment," "analog," "derivative," or "variant" when referring to a GLP-1/glucagon agonist peptide includes any peptide which retains at least some desirable activity, e.g., binding to glucagon and/or GLP-1 receptors. Fragments of GLP-1/glucagon agonist peptides provided herein include proteolytic fragments, deletion fragments which exhibit desirable properties during expression, purification, and or administration to an subject.

The term "variant," as used herein, refers to a peptide that differs from the recited peptide due to amino acid substitutions, deletions, insertions, and/or modifications. Variants can be produced using art-known mutagenesis techniques. Variants can also, or alternatively, contain other modifications—for example a peptide can be conjugated or coupled, e.g., fused to a heterologous amino acid sequence or other moiety, e.g., for increasing half-life, solubility, or stability. Examples of moieties to be conjugated or coupled to a peptide provided herein include, but are not limited to, albumin, an immunoglobulin Fc region, polyethylene glycol (PEG), and the like. The peptide can also be conjugated or produced coupled to a linker or other sequence for ease of synthesis, purification or identification of the peptide (e.g., 6-His), or to enhance binding of the polypeptide to a solid support.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10), and any other required parameter including but not limited to matrix option.

The terms "composition" or "pharmaceutical composition" refer to compositions containing a GLP-1/glucagon agonist peptide provided herein, along with e.g., pharmaceutically acceptable carriers, excipients, or diluents for administration to a subject in need of treatment, e.g., a human subject being treated for obesity.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

An "effective amount" is that amount of a GLP-1/glucagon agonist peptide provided herein, the administration of which to a subject, either in a single dose or as part of a series, is effective for treatment, e.g., treatment of obesity. An amount is effective, for example, when its administration results in one or more of weight loss or weight maintenance (e.g., prevention of weight gain), loss of body fat, prevention or modulation hypoglycemia, prevention or modulation hyperglycemia, promotion of insulin synthesis, or reduction in food intake. This amount can be a fixed dose for all subjects being treated, or can vary depending upon the weight, health, and physical condition of the subject to be treated, the extent of weight loss or weight maintenance desired, the formulation of peptide, a professional assessment of the medical situation, and other relevant factors.

The term "subject" is meant any subject, particularly a mammalian subject, in need of treatment with a GLP-1/glucagon agonist peptide provided herein. Mammalian subjects include, but are not limited to, humans, dogs, cats, guinea pigs, rabbits, rats, mice, horses, cattle, bears, cows, apes, monkeys, orangutans, and chimpanzees, and so on. In one embodiment, the subject is a human subject.

As used herein, an "subject in need thereof" refers to an individual for whom it is desirable to treat, e.g., to an obese subject or a subject prone to obesity for whom it is desirable to facilitate weight or body fat loss, weight or body fat maintenance, or to prevent or minimize weight gain over a specified period of time.

As used herein a "GLP-1/glucagon agonist peptide" is a chimeric peptide that exhibits activity at the glucagon receptor of at least about 1%, 5%, 10%, 20%, 30%, 40%, 50%, 60%, 70%, 80%, 90%, 95%, or more relative to native glucagon and also exhibits activity at the GLP-1 receptor of about at least about 1%, 5%, 10%, 20%, 30%, 40%, 50%, 60%, 70%, 80%, 90%, 95%, or more relative to native GLP-1, under the conditions of assay 1.

As used herein the term "native glucagon" refers to naturally-occurring glucagon, e.g., human glucagon, comprising the sequence of SEQ ID NO: 1. The term "native GLP-1" refers to naturally-occurring GLP-1, e.g., human GLP-1, and is a generic term that encompasses, e.g., GLP-1(7-36) amide (SEQ ID NO: 2), GLP-1(7-37) acid (SEQ ID NO: 3) or a mixture of those two compounds. As used herein, a general reference to "glucagon" or "GLP-1" in the absence of any further designation is intended to mean native human glucagon or native human GLP-1, respectively. Unless otherwise indicated, "glucagon" refers to human glucagon, and "GLP-1" refers to human GLP-1.

GLP-1/Glucagon Agonist Peptides

Provided herein are peptides which bind both to a glucagon receptor and to a GLP-1 receptor. In certain embodiments, the peptides provided herein are co-agonists of glucagon and GLP-1 activity. Such peptides are referred to herein as GLP-1/glucagon agonist peptides. GLP-1/glucagon agonist peptides as provided herein possess GLP-1 and glucagon activities with favorable ratios to promote weight loss, prevent weight gain, or to maintain a desirable body weight, and possess optimized solubility, formulatability, and stability. In certain embodiments, GLP-1/glucagon agonist peptides as provided herein are active at the human GLP1 and human glucagon receptors, in certain embodiment relative activity compared to the natural ligand at the GLP-1 receptor is at least about 1-fold, 2-fold 5-fold, 8-fold, 10-fold, 15-fold, 20-fold, or 25-fold higher than at the glucagon receptor.

In certain embodiments, GLP-1/glucagon agonist peptides as disclosed have desirable potencies at the glucagon and GLP-1 receptors, and have desirable relative potencies for promoting weight loss. In certain embodiments, GLP-1/glucagon agonist peptides as disclosed exhibit in vitro potencies at the GLP-1 receptor as shown by an EC50 in the cAMP assay 1 (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the GLP-1 receptor as shown by EC50 in the cAMP assay in 4.4% human serum albumin (assay 2, see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the glucagon receptor as shown by an EC50 in the cAMP assay 1 (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the glucagon receptor as shown by an EC50 in the cAMP assay in 4.4% human serum albumin (assay 2, see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed have relative GLP1-R/glucR potency ratios, when compared to the native ligands, in the range of about 0.01 to 0.50, e.g., from about 0.02 to 0.30, e.g., about 0.02, 0.03, 0.04, 0.05, 0.06, 0.07, 0.08, 0.09, 0.10, 0.11. 0.12, 0.13, 0.14, 0.15, 0.16, 0.17, 0.18, 0.19, 0.20, 0.21, 0.22, 0.23, 0.24, 0.25, 0.26, 0.27, 0.28, or 0.30. when using assay 2.

In certain embodiments, GLP-1/glucagon agonist peptides as disclosed exhibit in vitro potencies at the glucose-dependent insulinotropic peptide (gastric inhibitory peptide) (GIPR) as shown by an EC50 in the cAMP assay 1 (see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM. In certain embodiments, GLP-1/glucagon agonist peptides as disclosed exhibit in vitro potencies at the GIPR as shown by EC50 in the cAMP assay in 4.4% human serum albumin (assay 2, see Example 2) of less than 10,000 pM, less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

In certain embodiments, GLP-1/glucagon agonist peptides provided herein possess one or more criteria of acceptable solubility, ease in formulatability, plasma stability, and improved pharmacokinetic properties. In certain embodiments, GLP-1/glucagon agonist peptides as disclosed are soluble in standard buffers over a broad pH range.

In certain embodiments, GLP-1/glucagon agonist peptides are soluble in common buffer solutions at a concentration up to 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, or more, in buffer systems and a range of ionic strengths, e.g., from 0.25 to 150 mM, including, but not limited to phosphate buffer, Tris buffer, glutamate buffer, acetate buffer, succinate buffer, or histidine buffer. Exemplary buffers include 100 mM glutamate pH 4.5 buffer, 100 mM acetate pH 5 buffer, 100 mM succinate pH 5 buffer, 100 mM phosphate pH 6 buffer, 100 mM histidine pH 6 buffer, 100 mM phosphate pH 6.5 buffer, 100 mM phosphate pH 7.0 buffer, 100 mM histidine pH 7.0 buffer, 100 mM phosphate pH 7.5 buffer, 100 mM Tris pH 7.5 buffer, and 100 mM Tris pH 8.0 buffer. In certain embodiments, GLP-1/glucagon agonist peptides as disclosed are soluble in standard buffers at 0.8 mg/ml over a range of pH, e.g., from pH 4.0 to pH 8.0, e.g., at pH 4.0, 4.5, 5.0, 5.5, 6.0, 6.5, 7.0, 7.5, 8.0, or 8.5. In certain embodiments, GLP-1/glucagon agonist peptides as disclosed are soluble in standard buffers from pH 4.5 to 8.0, 5.0 to 8.0, 5.5 to 8.0, 6.0 to 8.0, 6.5 to 8.0, 7.0 to 8.0, 4.5 to 8.5, 5.5 to 8.5, 5.5 to 8.5, 6.0 to 8.5, 6.5 to 8.5, or 7.0 to 8.5.

In certain embodiments, GLP-1/glucagon agonist peptides as disclosed are formulatable in standard pharmaceutical formulations. Exemplary formulations include, but are not limited to: 0.1M Tris pH 7.5, 150 mM Mannitol, final formulation pH=7.2; 0.05M Tris, 50 mM Arginine/Proline, final formulation pH=8.0; or sodium phosphate buffer (pH8)/1.85% W/V propylene glycol, final formulation pH=7.0. In certain embodiments GLP-1/glucagon agonist peptides as disclosed are soluble is these or other formulations at a concentration up to 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, or more.

In certain embodiments, GLP-1/glucagon agonist peptides as disclosed are acceptably stable against proteases in serum or plasma. Common degradation products of glucagon or GLP-1 include +1 products (acid) and the DPP IV-cleavage products. Products with +1 mass may arise from deamidation at amide groups of glutamine or at the C-terminus. Cleavage products arise from the action of the protease DPP IV in plasma. In certain embodiments, GLP-1/glucagon agonist peptides as disclosed are remain stable in plasma at levels up to 30%, 40%, 50%, 60%, 70%, 80%, 90%, or 100% after 24 hours in plasma at 37° C.

Provided herein is a GLP-1/glucagon agonist peptide comprising the amino acid sequence:

HX2QGTFTSDX10SX12X13LX15X16X17X18AX20X21FX23X24
WLX27X28GX30;

wherein X2 is G or S, X10 is Y or K, X12 is K, E, R, or S, X13 is K or Y, X15 is D or E. X16 is S or G, X17 is E, R, Q, or K, X18 is R, S, or A, X20 is R, K, or Q, X21 is D or E, X23 is V or I, X24 is A or Q, X27 is E or V, X28 is A or K, and X30 is G or R. (SEQ ID NO:4). In certain embodiments the isolated peptide shown above is provided, where X2 is S, X10 is Y or K, X12 is K, E, R, or S, X13 is K or Y, X15 is D, X16 is S, X17 is E, R, Q, or K, X18 is R, S, or A, X20 is R, X21 is D, X23 is V, X24 is A, X27 is E or V, X28 is A, and X30 is G (SEQ ID NO:5). In certain embodiments the isolated peptide shown above is provided, where X2 is S, X10 is Y or K, X12 is K, E, R, or S, X13 is K or Y, X15 is D, X16 is S, if X17 is E and X18 is R, or if X17 is R and X18 is S, X20 is R, X21 is D, X23 is V, X24 is A, X27 is E or V, X28 is A, and X30 is G (SEQ ID NO: 6 and SEQ ID NO. 7, respectively). In certain embodiments the isolated peptide shown above is provided, where X2 is S, X10 is Y, X12 is K, X13 is K, X15 is D, X16 is S, if X17 is E and X18 is R, or if X17 is R and X18 is S, X20 is R, X21 is D, X23 is V, X24 is A, X27 is V, X28 is A, and X30 is G (SEQ ID NO: 8 and SEQ ID NO: 9, respectively). In certain embodiments the isolated peptide shown above is provided, where X2 is S, X10 is K, X12 is K, E, R, or S, X13 is Y, X15 is D, X16 is S, if X17 is E and X18 is R, and if X17 is R and X18 is S, X20 is R, X21 is D, X23 is V, X24 is A, X27 is E, X28 is A, and X30 is G (SEQ ID NO: 10 and SEQ ID NO: 11, respectively). In certain embodiments the isolated peptide shown above is provided, where X2 is S, X10 is K, X12 is E, X13 is Y, X15 is D, X16 is S, if X17 is E and X18 is R, or if X17 is R and X18 is S, X20 is R, X21 is D, X23 is V, X24 is A, X27 is E, X28 is A, and X30 is G (SEQ ID NO: 12 and SEQ ID NO: 13, respectively). In certain embodiments the isolated peptide shown above is provided, where X2 is S, X10 is K, X12 is R, X13 is Y, X15 is D, X16 is S, if X17 is E and X18 is R, or if X17 is R and X18 is S, X20 is R, X21 is D, X23 is V, X24 is A, X27 is E, X28 is A, and X30 is G (SEQ ID NO: 14 and SEQ ID NO: 15, respectively).

GLP-1/glucagon agonist peptides provided herein include, but are not limited to G730 (SEQ ID NO: 16), G797 (SEQ ID NO: 17), G849 (SEQ ID NO: 18), G933 (SEQ ID NO: 19), G865 (SEQ ID NO: 20), G796 (SEQ ID NO: 21), G812 (SEQ ID NO: 22) and G380 (SEQ ID NO: 23). These GLP-1/glucagon agonist peptides are listed in Table 1:

TABLE 1

| GLP-1/Glucagon Peptide Sequences | | |
|---|---|---|
| Peptide | Sequence | SEQ ID NO: |
| G730 | HSQGT FTSDY SKXLD SERAR DFVAW LVAGG-amide X13 = K(gE-palm) | 16 |
| G797 | HSQGT FTSDX SEYLD SERAR DFVAW LEAGG-amide X10 = K(gE-palm) | 17 |
| G849 | HSQGT FTSDX SRYLD SRSAR DFVAW LEAGG-amide X10 = K(gE-palm) | 18 |
| G933 | HSQGT FTSDX SEYLD SERAR DFVAW LEAGG-acid X10 = K(gE-palm) | 19 |
| G865 | HSQGT FTSDX SSYLD SRSAR DFVAW LEAGG-amide X10 = K(gE-palm) | 20 |
| G796 | HSQGT FTSDX SSYLD SRRAR DFVAW LEAGG-amide X10 = K(gE-palm) | 21 |
| G812 | HSQGT FTSDX SKYLE GQAAK EFIAW LEKGR-amide X10 = K(gE-palm) | 22 |
| G380 | HGQGT FTSDY SKYLD SXRAQ DFVQW LVAGG-amide X17 = K(gE-palm) | 23 |
| G931 | HSQGT FTSDY SKXLD SERAR DFVAW LVAGG-acid X13 = K(gE-palm) | 24 |
| G934 | HSQGT FTSDX SKYLE GQAAK EFIAW LEKGR-acid X10 = K(gE-palm) | 25 |
| G973 | HSQGT FTSDX SSYLD SRSAR DFVAW LEAGG-acid X10 = K(gE-palm) | 26 |

TABLE 1-continued

GLP-1/Glucagon Peptide Sequences

| Peptide | Sequence | SEQ ID NO: |
|---|---|---|
| GLP1 | HAEGT FTSDV SSYLE GQAAK EFIAW LVKGR | SEQ ID NO: 2 (7-36 amide)/SEQ ID NO:3 (7-37 acid) |
| Glucagon | HSQGT FTSDY SKYLD SRRAQ DFVQW LT | SEQ ID NO: 1 |

K(gE-Palm) = Lysine with a palmitoyl group conjugated to the epsilon nitrogen, through a gamma glutamic acid linker.

The peptides G797 and G933 both have a glutamate residue at position 12, and maintain robust activity at both the glucagon and GLP-1 receptors, as shown in Example 2. The corresponding residue is lysine in exendin-4 and glucagon and is serine in GLP-1. Although this residue is not thought to contact the receptor, changes in charge from positive to negative may modify the adjacent environment. Furthermore, G797, G849 and G933 have a glutamate residue at position 27. Residue 27 is Lysine in exendin 4 and is an uncharged hydrophobic residue in GLP1 (valine) and glucagon (methionine). The lysine of exenatide makes electrostatic interactions with the GLP1 receptor at residues Glu127 and Glu24 (C. R. Underwood et al *J Biol Chem* 285 723-730 (2010); S. Runge et al *J Biol Chem* 283 11340-11347 (2008)). While a loss of GLP1R potency might be expected when the charge at position 27 is changed to negative, the change is compatible with GLP1R activity in G797, G849, and G933.

Methods of Making.

This disclosure provides a method of making a GLP-1/glucagon agonist peptide. GLP-1/glucagon agonist peptides provided herein can be made by any suitable method. For example, in certain embodiments the GLP-1/glucagon agonist peptides provided herein are chemically synthesized by methods well known to those of ordinary skill in the art, e.g., by solid phase synthesis as described by Merrifield (1963, *J. Am. Chem. Soc.* 85:2149-2154). Solid phase peptide synthesis can be accomplished, e.g., by using automated synthesizers, using standard reagents, e.g., as explained in Example 1.

Alternatively, GLP-1/glucagon agonist peptides provided herein can be produced recombinantly using a convenient vector/host cell combination as would be well known to the person of ordinary skill in the art. A variety of methods are available for recombinantly producing GLP-1/glucagon agonist peptides. Generally, a polynucleotide sequence encoding the GLP-1/glucagon agonist peptide is inserted into an appropriate expression vehicle, e.g., a vector which contains the necessary elements for the transcription and translation of the inserted coding sequence. The nucleic acid encoding the GLP-1/glucagon agonist peptide is inserted into the vector in proper reading frame. The expression vector is then transfected into a suitable host cell which will express the GLP-1/glucagon agonist peptide. Suitable host cells include without limitation bacteria, yeast, or mammalian cells. A variety of commercially-available host-expression vector systems can be utilized to express the GLP-1/glucagon agonist peptides described herein.

Modifications, Conjugates, Fusions, and Derivations.

In certain embodiments, GLP-1/glucagon agonist peptides provided herein are stabilized via amino acid modifications. In certain embodiments, the carboxyl group of the C-terminal amino acid is amidated. In certain embodiments, the C-terminal amino acid is amidated glycine, e.g., G730, G797, G849, G865, G796, G812, and G380. In certain embodiments, e.g., G933, the C-terminal glycine is the unmodified acid. In certain embodiments, GLP-1/glucagon agonist peptides are provided in which one or more amino acid residues are acylated. For example, in certain embodiments GLP-1/glucagon agonist peptides provided herein contain one or more lysine residues, in which a palmitoyl moiety is attached to the N(epsilon) group. In certain embodiments a linker is incorporated between lysine and the palmitoyl group. This linker can be a gamma glutamic acid group, or an alternative linker such as, but not limited to, beta alanine and aminohexanoic acid. Different acylation methods may be used such as addition of cholesterol or myristoyl groups. In certain embodiments, the palmitoyl moiety is added at position 13 (e.g., G730). In certain embodiments, the palmitoyl moiety is added at position 10 (e.g., G797, G849, G933, G865, G796, and G812). In certain embodiments, the palmitoyl moiety is added at position 17 (e.g., G380).

The GLP-1/glucagon agonist peptides provided herein, e.g., G730, G797, G849 and G933 can be palmitoylated to extend their half-life by association with serum albumin, thus reducing their propensity for renal clearance, as described in Example 1.

Alternatively or in addition, a GLP-1/glucagon agonist peptide as disclosed herein can be associated with a heterologous moiety, e.g., to extend half-life. The heterologous moiety can be a protein, a peptide, a protein domain, a linker, an organic polymer, an inorganic polymer, a polyethylene glycol (PEG), biotin, an albumin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of such moieties.

For example, GLP-1/glucagon agonist peptides can be fused with a heterologous polypeptide. The peptides can be fused to proteins, either through recombinant gene fusion and expression or by chemical conjugation. Proteins that are suitable as partners for fusion include, without limitation, human serum albumin, antibodies and antibody fragments including fusion to the Fc portion of the antibodies. GLP-1 has been fused to these proteins with retention of potency (L.

Baggio et al, *Diabetes* 53 2492-2500 (2004); P. Barrington et al *Diabetes, Obesity and Metabolism* 13 426-433 (2011); P. Paulik et al American Diabetes Association 2012, Poster 1946). Extended recombinant peptide sequences have also been described to give the peptide high molecular mass (V. Schellenberger et al *Nature Biotechnol* 27 1186-1190 (2009); PASylation (EP2173890)). In certain embodiments GLP-1/glucagon agonist peptides are incorporated as the N-terminal part of a fusion protein, with the fusion partner, e.g., the albumin or Fc portion, at the C-terminal end. GLP-1/glucagon agonist peptides as described herein can also be fused to peptides or protein domains, such as 'Albudabs' that have affinity for human serum albumin (M. S. Dennis et al *J Biol Chem* 277 35035-35043 (2002); A. Walker et al Protein Eng Design Selection 23 271-278 (2010)). Methods for fusing a GLP-1/glucagon agonist peptides as disclosed herein with a heterologous polypeptide, e.g., albumin or an Fc region, are well known to those of ordinary skill in the art.

Other heterologous moieties can be conjugated to GLP-1/glucagon agonist peptides to further stabilize or increase half-life. For chemical fusion, certain embodiments feature maintenance of a free N-terminus, but alternative points for derivatization can be made. A further alternative method is to derivatize the peptide with a large chemical moiety such as high molecular weight polyethylene glycol (PEG). A "pegylated GLP-1/glucagon agonist peptide" has a PEG chain covalently bound thereto. Derivatization of GLP-1/glucagon agonist peptides, e.g., pegylation, can be done at the lysine that is palmitoylated, or alternatively at a residue such as cysteine, that is substituted or incorporated by extension to allow derivatization. GLP-1/glucagon agonist peptide formats above can be characterized in vitro and/or in vivo for relative potency and the balance between GLP-1 and glucagon receptor activation.

The general term "polyethylene glycol chain" or "PEG chain", refers to mixtures of condensation polymers of ethylene oxide and water, in a branched or straight chain, represented by the general formula $H(OCH_2CH_2)_nOH$, where n is an integer of 3, 4, 5, 6, 7, 8, 9, or more. PEG chains include polymers of ethylene glycol with an average total molecular weight selected from the range of about 500 to about 40,000 Daltons. The average molecular weight of a PEG chain is indicated by a number, e.g., PEG-5,000 refers to polyethylene glycol chain having a total molecular weight average of about 5,000.

PEGylation can be carried out by any of the PEGylation reactions known in the art. See, e.g., Focus on Growth Factors, 3: 4-10, 1992 and European patent applications EP 0 154 316 and EP 0 401 384. PEGylation may be carried out using an acylation reaction or an alkylation reaction with a reactive polyethylene glycol molecule (or an analogous reactive water-soluble polymer).

Methods for preparing a PEGylated GLP-1/glucagon agonist peptides generally include the steps of (a) reacting a GLP-1/glucagon agonist peptide or with polyethylene glycol (such as a reactive ester or aldehyde derivative of PEG) under conditions whereby the molecule becomes attached to one or more PEG groups, and (b) obtaining the reaction product(s).

Pharmaceutical Compositions

Further provided are compositions, e.g., pharmaceutical compositions, that contain an effective amount of a GLP-1/glucagon agonist peptide as provided herein, formulated for the treatment of metabolic diseases, e.g., obesity.

Compositions of the disclosure can be formulated according to known methods. Suitable preparation methods are described, for example, in *Remington's Pharmaceutical Sciences*, 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the invention can be administered directly to the subject.

Carriers that can be used with compositions of the invention are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Method of Treating Obesity, Model Systems.

GLP-1/glucagon agonist peptides can combine the effect of glucagon e.g., inhibition of food intake or regulation of glucose levels with the effect of GLP-1 e.g., inhibition of gastric motility, or promotion of insulin release. They can therefore act to accelerate elimination of excessive adipose tissue, induce sustainable weight loss, and improve glycemic control. GLP-1/glucagon agonist peptides can also act to reduce cardiovascular risk factors such as high cholesterol, and high LDL-cholesterol or abnormal HDL/LDL ratios.

This disclosure provides a method of treating obesity or an obesity-related disease or disorder, comprising administering to a subject in need of treatment a GLP-1/glucagon agonist peptide as disclosed herein. Further provided is a GLP-1/glucagon agonist peptide for treatment of obesity or an obesity-related disease or disorder. Further provided is use of a GLP-1/glucagon agonist peptide as provided herein in the manufacture of a medicament for the treatment of obesity or an obesity-related disease or disorder.

GLP-1/glucagon agonist peptides provided herein can be administered for preventing weight gain, promoting weight loss, reducing excess body weight or treating obesity (e.g. by control of appetite, feeding, food intake, calorie intake, and/or energy expenditure), including morbid obesity. In addition, GLP-1/glucagon agonist peptides provided herein can be used for treatment of other obesity-related metabolic disorders. Examples of other obesity-related disorders include without limitation: insulin resistance, glucose intolerance, pre-diabetes, increased fasting glucose, type 2 diabetes, hypertension, dyslipidemia (or a combination of these metabolic risk factors), glucagonomas, cardiovascular diseases such as congestive heart failure, atherosclerois, arteriosclerosis, coronary heart disease, or peripheral artery disease, stroke, respiratory dysfunction, or renal disease.

"Treatment" is an approach for obtaining beneficial or desired clinical results. As provided herein, beneficial or desired clinical results from the disclosed GLP-1/glucagon agonist peptides include, without limitation, reduced body weight, decreased weight-gain, reduced appetite, reduced or stabilized serum glucose and serum insulin levels, amelioration, palliation, stabilization, diminishment of extent of obesity-related diseases, or a delay or slowing of obesity-related disease progression. "Treatment" refers to both therapeutic treatment and prophylactic or preventative measures in certain embodiments. Those in need of treatment include those already with the disorder as well as those in which the disorder is to be prevented. By treatment is meant inhibiting or reducing an increase in obesity-related symptoms (e.g. weight gain) when compared to the absence of treatment, and is not necessarily meant to imply complete cessation of the relevant condition.

The route of administration of GLP-1/glucagon agonist peptides provided herein can be, for example, oral, parenteral, by inhalation or topical. The term parenteral as used herein includes, e.g., intravenous, intraarterial, intraperitoneal, intramuscular, subcutaneous, rectal, or vaginal administration. Another example of a form for administration is a solution for injection, in particular for intravenous or intraarterial injection or drip. GLP-1/glucagon agonist peptides provided herein can be administered as a single dose or as multiple doses. In certain embodiments, a GLP-1/glucagon agonist peptide is administered by subcutaneous injection.

Parenteral formulations can be a single bolus dose, an infusion or a loading bolus dose followed with a maintenance dose. These compositions can be administered at specific fixed or variable intervals, e.g., once a day, or on an "as needed" basis. Dosage regimens also can be adjusted to provide the optimum desired response (e.g., a therapeutic or prophylactic response).

The amount of a GLP-1/glucagon agonist peptide to be administered can be readily determined by one of ordinary skill in the art without undue experimentation given the disclosure herein. Factors influencing the mode of administration and the respective amount of a GLP-1/glucagon agonist peptide include, but are not limited to, the severity of the disease (e.g., the extent of obesity), the subject's history, and the age, height, weight, health, and physical condition of the subject undergoing therapy. Similarly, the amount of a GLP-1/glucagon agonist peptide to be administered will be dependent upon the mode of administration and whether the subject will undergo a single dose or multiple doses of this agent. In certain embodiments, GLP-1/glucagon agonist peptides provided herein can be administered once per day via injection.

Kits

In yet other embodiments, the present disclosure provides kits comprising GLP-1/glucagon agonist peptides, that can be used to perform the methods described herein. In certain embodiments, a kit comprises a GLP-1/glucagon agonist peptide disclosed herein in one or more containers. One skilled in the art will readily recognize that the disclosed GLP-1/glucagon agonist peptides can be readily incorporated into one of the established kit formats which are well known in the art.

EXAMPLES

Example 1: Synthesis, Modifications, and Characterization of GLP-1/Glucagon Agonist Peptides

LIST OF ABBREVIATIONS

Boc: tert-butyloxycarbonyl
tert-Bu; tert-butyl
DCM: dichloromethane
DIC: diisopropylcarbodiimide
Fmoc: 9-fluorenylmethoxycarbonyl
HOBt: 1-hydroxybenzotriazole
HPLC: High Performance Liquid Chromatography
Mtt: 4-methyltrityl
NMP: N-methylpyrrolidone
Pbf: 2,2,4,6,7-pentamethyldihydrobenzofuran-5-sulfonyl
TFA: trifluoroacetic acid
TIS: triisopropylsilane
Trt: triphenylmethyl, trityl GLP-1/glucagon agonist peptides were synthesized as follows. Elongation of peptide chains on NovaSyn TGR or preloaded Fmoc-Wang resin (NovaBiochem) was performed with a PRELUDE™ solid phase peptide synthesizer (Protein Technologies, Tucson, Ariz., USA). Manufacturer-supplied protocols were applied for coupling of the hydroxybenzotriazole esters of amino acids in N-methylpyrolidone (NMP). The fluorenylmethoxycarbonyl (Fmoc) group was used for the semipermanent protection of alpha-amino groups of amino acids, whereas the side chains were protected with tert-butyl (tert-Bu) for serine, threonine, aspartic acid, glutamic acid, tyrosine, and 2,2,4,6,7-pentamethyldihydrobenzofuran-5-sulfonyl (Pbf) for arginine, and trityl (Trt) for histidine. The N-terminal amino group of histidine in position 1 was protected with tert-butyloxycarbonyl group (Boc). Lys(Mtt) was incorporated into the peptide chain when a subsequent chemical modification of the side chain was required.

Upon completion of the peptide chain elongation, the Mtt group was removed by washing the peptide-resin with DCM containing 2% TFA and 5% TIS (10×7 ml, each 0.5 min). Coupling of a lipid moiety to the side chain of Lys was performed on the PRELUDE™ peptide synthesizer using DIC as a coupling reagent in the presence of HOBt.

Peptides were cleaved from the resin using mixture of TFA:TIS:water (95:2.5:2.5). After 2 h at room temperature, the peptidyl resin was filtered, washed with TFA and combined filtrates were evaporated to dryness in vacuo. The residue was triturated with ether, and the precipitate which formed was filtered, washed with ether, and dried. The crude peptides were dissolved in 5% acetic acid in water and analyzed by reverse-phase high-pressure liquid chromatography on a Polaris 3 C8-A column attached to Varian 920-LC system. A standard gradient system of 10 to 90% buffer B over the course of 15 min was used for analysis. Buffer A was 0.1% TFA in water and buffer B was 0.1% TFA in acetonitrile. HPLC profiles were recorded at 210 nm. Preparative separations were performed on Varian ProStar system with a semipreparative C18 RP XBridge Waters column. The above-described solvent system of water and acetonitrile, in a gradient of 30 to 70% buffer B over the course of 30 min, was used for separation. The chromatographically homogenous products (>97% pure) were analyzed by electrospray mass spectrometry (MassLynx, Waters).

Example 2: In Vitro Studies

Glucagon and GLP-1 Receptor Mediated cAMP Production

Biological Activity of Peptides in Cell-Based cAMP Activity Assay (Assay 1):

The biological activity of GLP-1/glucagon agonist peptides synthesized by the method of Example 1 were tested for biological activity, e.g., stimulation of one or more cellular receptor responses, by the following methods. Stable cell lines expressing human, mouse, rat, or dog GLP-1 receptor (GLP-1R), glucagon receptor (GCGR) or glucose-dependent insulinotropic peptide (gastric inhibitory polypeptide) receptor (GIPR) were generated in HEK293s or CHO cells by standard methods. Peptide activation of these various receptors results in downstream production of cAMP second messenger which can be measured in a functional activity assay.

cAMP assays were performed using "assay medium":
Assay Medium: 10% FBS in DMEM (Gibco #41966), containing 0.5 mM IBMX (Sigma #I7018).

Low protein binding 384-well plates (Greiner #781280) were used to perform eleven 1 in 5 serial dilutions of test samples which were made in assay medium. All sample dilutions were made in duplicate.

A frozen cryo-vial of cells expressing the receptor of interest was thawed rapidly in a water-bath, transferred to pre-warmed assay media and spun at 240×g for 5 minutes. Cells were re-suspended in assay media at an optimised concentration (e.g. hGCGR cells at $1\times10^5$ cells/ml, hGLP-1R and hGIPR cells at $0.5\times10^5$ cells/ml).

From the dilution plate, a 5 μL replica was stamped onto a black shallow-well u-bottom 384-well plate (Corning #3676). To this, 5 μL cell suspension was added and the plates incubated at room temperature for 30 minutes.

cAMP levels were measured using a commercially available cAMP dynamic 2 HTRF kit (Cisbio, Cat #62AM4PEJ), following the two step protocol as per manufacturer's recommendations. In brief; anti-cAMP cryptate (donor fluorophore) and cAMP-d2 (acceptor fluorophore) were made up separately by diluting each 1/20 in conjugate & lysis buffer provided in the kit. 5 μL anti-cAMP cryptate was added to all wells of the assay plate, and 5 μL cAMP-d2 added to all wells except non-specific binding (NSB) wells, to which conjugate and lysis buffer was added. Plates were incubated at room temperature for one hour and then read on an Envision (Perkin Elmer) using excitation wavelength of 320 nm and emission wavelengths of 620 nm & 665 nm.

Sequences of synthesized GLP-1/glucagon agonist peptides and their EC50 values determined in cAMP assays, performed in "assay medium," are shown in Table 2. All peptides in Table 2 were synthesized with a C-terminal amide. Additional GLP-1/glucagon agonist peptides were synthesized with a C-terminal acid and EC50 values determined in cAMP assays, performed in "assay medium," are shown in Table 3. EC50 for additional GLP-1/glucagon agonist peptides, performed in "assay medium," are shown in Table 4. All peptides in Table 4 have a C-terminal amide, unless they are denoted as 'acid' in which case they have a C-terminal acid.

TABLE 2 cAMP activity of GLP-1/glucagon agonist peptides with C-terminal amide (assay 1)

| | Assay in Assay Medium | | |
| --- | --- | --- | --- |
| Peptide | Human GlucR EC50 M | Human GLP1R EC50 M | Human GIPr EC50 M |
| G730 | 6.23E−12 | 1.8E−11 | 4.5E−08 |
| G797 | 6.14E−12 | 1.4E−11 | 3.4E−09 |
| G849 | 2.26E−12 | 9.0E−12 | 1.7E−08 |
| G865 | 1.26E−11 | 8.3E−12 | 2.2E−08 |
| G796 | 1.76E−12 | 1.3E−11 | 1.4E−08 |
| G812 | 8.17E−12 | 1.1E−11 | 2.7E−09 |
| G380 | 2.17E−10 | 7.7E−11 | 1.3E−07 |
| GLP1 | | 8.1E−11 | |
| Glucagon | 3.3E−12 | | |

TABLE 3 cAMP activity of GLP-1/glucagon agonist peptides with C-terminal acid (assay 1)

| Peptide | Human GlucR EC50 M | Human GLP1R EC50 M | Human GIPr EC50 M |
| --- | --- | --- | --- |
| G931 | 1.78E−11 | 1.30E−10 | 0.00E+00 |
| G933 | 5.92E−12 | 3.20E−11 | 9.70E−09 |
| G934 | 6.30E−12 | 1.80E−11 | 3.60E−09 |
| G973 | 8.90E−12 | 1.20E−11 | 4.70E−08 |

TABLE 4 cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
| --- | --- | --- | --- | --- |
| Parent sequence HSQGT FTSDY SKYLD SRRAQ DFVQW LVAGG Peptides in this section all contain LVAGG at residues 26 to 30 | | | | |
| Glucagon | 3.3E−12 | 4.2E−09 | 1.99E−07 | |
| GLP1 | 1.53E−07 | 8.1E−11 | 1.53E−07 | |
| g715 | 2.53E−12 | 2.04E−11 | 9.98E−10 | K(gE-palm)10 |
| g716 | 2.46E−09 | 1.29E−08 | 1.18E−08 | K(gEpalm)11 |
| g702 | 1.49E−09 | 3.35E−09 | 0.00E+00 | K(gEpalm)12, E17 |
| g728 | 2.44E−09 | 1.69E−10 | 3.95E−07 | K(gEpalm)12, E17 R20 A24 |
| g729 | 3.19E−11 | 7.29E−11 | 2.09E−07 | K(gEpalm)13 E17 |
| g730 | 1.50E−11 | 3.95E−11 | 5.66E−08 | K(gEpalm)13 E17 R20 A24 |

TABLE 4-continued cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| g875 | 1.29E-10 | 2.98E-11 | 2.90E-08 | K(gEpalm)13 R20 A24, E17 Aib2 |
| g841 | no data | | | K(gEpalm)13 R20 A24, S18 R12 acid |
| g802 | 1.81E-09 | 9.64E-11 | 9.12E-08 | K(gEpalm)13, R20 A24, E17, E12 |
| g820 | 1.17E-11 | 3.39E-11 | 7.11E-08 | K(gEpalm)13, R20 A24, E17, R12 |
| g842 | 8.31E-12 | 5.12E-11 | 8.83E-08 | K(gEpalm)13, R20 A24, E17, R12 acid |
| g733 | 6.20E-08 | 2.31E-11 | 8.17E-07 | K(gEpalm)14, G2 E3 |
| g803 | 1.08E-11 | 2.96E-11 | 3.29E-08 | K(gEpalm)14, R20 E24, S18 |
| g843 | no data | | | K(gEpalm)14, R20 A24, S18 R12 acid |
| g732 | 3.96E-11 | 2.32E-11 | 2.94E-08 | K(gEpalm)14, R20 A24, E17 G2 |
| g777 | 1.24E-12 | 2.74E-11 | 4.53E-09 | K(gEpalm)14, R20 A24, E17 |
| g844 | no data | | | K(gEpalm)14, R20 A24, E17 R12 Aib2 acid |
| g845 | no data | | | K(gEpalm)14, R20 A24, E17 R12 acid |
| g821 | 4.63E-12 | 5.58E-11 | 1.40E-08 | K(gEpalm)14, R20 A24, E17, R12 |
| g846 | 3.41E-11 | 4.38E-11 | 1.18E-08 | K(gEpalm)14, R20 A24, E17, E12 |
| g731 | 2.77E-11 | 4.22E-11 | 4.07E-08 | K(gEpalm)14, E12 |
| g670 | 8.00E-12 | 2.03E-11 | 1.49E-08 | K(gEpalm)14, S18 |
| g335 | 1.05E-11 | 7.33E-11 | 5.82E-07 | K(gE-palm)17 |
| g336 | 1.77E-12 | 3.66E-11 | 1.96E-08 | K(gE-gE-palm)17 |
| g384 | 4.29E-11 | 2.72E-11 | 1.70E-08 | K(gEpalm)17, Aib2 |
| g380 | 3.62E-10 | 1.00E-10 | 6.09E-07 | K(gEpalm)17, G2 |
| g736 | 9.19E-10 | 8.54E-11 | 0.00E+00 | K(gEpalm)17, G2, A20 A24 |
| g381 | 1.93E-09 | 9.08E-11 | 5.45E-07 | K(gEpalm)17, E3 |
| g678 | 4.52E-09 | 1.06E-10 | 1.23E-07 | K(gEpalm)17, G2 E20 |
| g599, g688 | 6.98E-11 | 1.20E-10 | 1.12E-07 | K(gEpalm)17, E20 |
| g679 | 1.89E-10 | 1.35E-10 | 1.17E-07 | K(gEpalm)17, G2 E24 |
| g600, g689 | 5.47E-12 | 6.66E-11 | 8.28E-08 | K(gEpalm)17, E24 |
| g680 | 3.68E-09 | 1.95E-10 | 9.67E-08 | K(gEpalm)17, G2 E20 E24 |
| g639 | 8.21E-08 | 2.44E-10 | 8.21E-08 | K(gEpalm)17, S2 E3 E20 E24 |
| g681 | 3.99E-08 | 2.83E-10 | 1.24E-07 | K(gEpalm)17, G2, E3 E20 E24 |
| g720 | 3.52E-10 | 5.34E-11 | 0.00E+00 | K(gEpalm)17, G2 R20 E24 R12 |
| g660 | 1.52E-09 | 1.06E-09 | 3.32E-07 | K(gEpalm)17, G2 R20 E24 |
| g835 | 4.24E-10 | 1.91E-10 | 9.72E-08 | K(gEpalm)17, R20 E24, E12 |
| g776 | 4.65E-12 | 7.02E-11 | 4.79E-08 | K(gEpalm)17, R20 E24 |
| g823 | 9.48E-12 | 9.73E-11 | 8.42E-08 | K(gEpalm)17, R20 E24, R12 |
| g867 | 7.04E-12 | 4.48E-11 | 4.17E-08 | K(gEpalm)17, R20 A24 |
| g736 | 9.20E-10 | 8.54E-11 | 0.00E+00 | K(gEpalm)17, A20 A24, G2 |
| g737 | 7.34E-07 | 8.14E-11 | 0.00E+00 | K(gEpalm)17, A20 A24, G2 E3 |
| g675 | 3.84E-08 | 1.51E-10 | 1.61E-06 | K(gEpalm)17, E12 R20 A24 G2 |

Parent sequence HSQGT FTSDY SKYLD SRRAQ DFVQW LEAGG Peptides in this section all have the sequence LEAGG from residue 26 onwards unless otherwise stated, e.g. LERGG

| g717 | 4.55E-13 | 5.77E-12 | 1.48E-09 | K(gEpalm)10, LEAGG |
| g796 | 1.81E-12 | 1.40E-11 | 1.74E-08 | K(gEpalm)10, LEAGG, R20 A24 S12 |
| g847 | no data | | | K(gEpalm)10, LEAGG, R20 A24 S18 E12 Aib2 acid |
| g797 | 9.64E-12 | 2.26E-11 | 4.64E-09 | K(gEpalm)10, LEAGG, R20 A24 E17 E12 |
| g798 | 5.10E-13 | 9.07E-12 | 1.51E-09 | K(gEpalm)10, LEAGG, R20 A24 E17 |

TABLE 4-continued cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| g848 | 9.66E−13 | 9.42E−12 | 2.77E−09 | K(gEpalm)10, LEAGG, R20 A24 E17 R12 |
| g849 | 2.28E−12 | 9.07E−12 | 1.81E−08 | K(gEpalm)10, LEAGG, R20 A24 S18 R12 |
| g701 | 3.83E−09 | 7.40E−09 | 0.00E+00 | K(gEpalm)12, LERGG, G2 E17 |
| g840 | 5.30E−12 | 1.45E−10 | 1.02E−07 | LEAGG, R20 A24, E17 |
| g824 | 1.05E−12 | 4.71E−11 | 5.74E−08 | K(gEpalm)14, LEAGG, R20, E24 |
| g780 | 7.92E−13 | 1.20E−11 | 6.40E−08 | K(gEpalm)14, LEAGG, R20 A24 |
| g601 | 4.93E−13 | 3.98E−11 | 7.41E−08 | K(gEpalm)14, LEAGG |
| g816 | 1.10E−12 | 3.16E−11 | 2.00E−08 | K(gEpalm)14, LEAGG, E17 |
| g817 | 1.68E−12 | 2.51E−11 | 1.52E−08 | K(gEpalm)14, LEAGG, A18 |
| g876 | 1.04E−11 | 8.63E−11 | 7.90E−08 | K(gEpalm)14, LEAGG, R20, E24, E12 |
| g805 | 1.44E−12 | 2.28E−11 | 9.97E−08 | K(gEpalm)14, LEAGG, R20 E24 |
| g850 | 2.19E−12 | 2.12E−11 | 8.96E−08 | K(gEpalm)14, LEA, R20, A24, S18 R12 |
| g836 | 1.55E−11 | 1.24E−10 | 1.00E−07 | K(gEpalm)14, LEAGG, R20 E24, E17 |
| g804 | 1.95E−12 | 7.15E−11 | 9.97E−08 | K(gEpalm)14, LEA, R20, A24 |
| g618 | no data | | | K(Ahx-palm)20, LEKGR |
| g781 | 2.86E−12 | 1.04E−10 | 4.02E−07 | K(gEpalm)16, LEAGG, R20 A24 |
| g782 | 1.56E−10 | 2.54E−11 | 1.43E−06 | K(gEpalm)18, LEAGG, R20 A24 |
| g744 | 3.92E−11 | 2.45E−09 | 0.00E+00 | K(gE-palm)20, LEAGG |
| g746 | 3.54E−11 | 1.15E−08 | 0.00E+00 | K(gE-palm)24, LEAGG |
| g747 | 9.42E−11 | 3.16E−09 | 1.04E−06 | K(gE-palm)31, LEAGG |
| g512 | 6.06E−11 | 9.80E−11 | 4.07E−07 | K(gEpalm)17, LEAGG, G2, |
| g513 | 7.23E−10 | 1.75E−10 | 2.98E−07 | K(gEpalm)17, LEAGG, E3, |
| g734 | 8.28E−08 | 6.95E−11 | 1.17E−06 | K(bA-palm)17, LEAGG, R20 A24, E3 E12 |
| g837 | 2.13E−10 | 4.67E−10 | 1.14E−07 | K(gE-palm)17, LEAGG, R20 A24 E12 |
| g838 | 5.68E−12 | 2.37E−11 | 8.43E−08 | K(Ahx-palm)17, LEAGG, R20 A24 E12 |
| g783 | 9.11E−11 | 4.24E−11 | 8.46E−07 | K(bA-palm)17, LEAGG, R20 A24 E12 |
| g851 | no data | | | K(bA-palm)17, LEAGG, R20 A24, R12 acid |
| g852 | no data | | | K(bA-palm)17, LEAGG, R20 A24, R12 Aib2 acid |
| g819 | 2.34E−12 | 1.80E−11 | 1.03E−07 | K(bA-palm)17, LEAGG, R20 A24 |
| g536 | 4.78E−12 | 7.45E−11 | 0.00E+00 | |
| g600 | 5.47E−12 | 6.66E−11 | 1.24E−07 | K(gE-palm)17, LVAGG, E24 |
| g599 | 9.62E−11 | 8.76E−11 | 1.13E−07 | K(gE-palm)17, LVAGG, E20 |

Parent sequence HSQGT5 FTSDY10 SKYLD15 SRRAQ20 DFVQW25 LERGG-amide
Peptides in this section all have the sequence LERGG from residue 26
onwards unless otherwise stated, e.g. LENT

| g825 | 3.67E−12 | 1.91E−11 | 8.67E−08 | K(Ahx-palm)17, LENT, R20 E24, E12 |
| g588 | 7.23E−11 | 1.10E−10 | 9.80E−08 | K(gEpalm)17, LERGG, G2, |
| g614 | 3.65E−12 | 9.31E−12 | 9.93E−08 | K(Ahx-palm)17, LERGG, E12 |
| g684 | 1.64E−10 | 1.51E−11 | 1.46E−07 | K(Ahx-palm)17, LERGG, R20 A24 E12 G2 |
| g721 | 3.23E−09 | 4.11E−10 | 9.79E−07 | K(gE-palm)17, LERGG, R20 A24 E12 G2 |
| g724 | 3.09E−08 | 1.90E−11 | 9.33E−07 | K(Ahx-palm)17, LERGG, R20 A24 E12 G2 E3 |
| g772 | 1.84E−10 | 2.92E−10 | 1.54E−06 | K(gE-palm)17, LERGG, R20 A24 E12 |
| g795 | 1.10E−10 | 7.34E−11 | 5.79E−07 | K(bA-palm)17, LERGG, R20 A24 E12 |
| g794 | 4.69E−12 | 1.57E−11 | 3.22E−08 | K(Ahx-palm)17, LERGG, R20 A24 E12 |
| g826 | 4.23E−12 | 2.93E−11 | 5.80E−08 | K(Ahx-palm)17, LERGG, R20 A24 E12 acid |
| g727 | 2.18E−10 | 2.63E−11 | 1.77E−07 | K(Ahx-palm)17, LERGG, R20 A24 E12 G2 acid |
| g683 | 3.72E−10 | 1.59E−11 | 1.26E−07 | K(Ahx-palm)17, LERGG, A20 A24 E12 G2 |
| g722 | 1.11E−08 | 4.26E−10 | 1.67E−06 | K(gE-palm)17, LERGG, A20 A24 E12 G2 |
| g725 | 5.99E−08 | 2.52E−11 | 1.48E−06 | K(Ahx-palm)17, LERGG, A20 A24 E12 G2 E3 |
| g818 | 8.90E−12 | 2.10E−11 | 9.40E−08 | K(Ahx-palm)17, LERGG, A20 A24 E12 |

TABLE 4-continued cAMP activity of additional GLP-1/glucagon agonist peptides (assay 1)

| | hGlucR EC50 M | hGLP1R EC50 M | hGIPR EC50 M | Site and nature of palmitoylation, Substitutions into parent sequence |
|---|---|---|---|---|
| g682 | 1.95E−10 | 1.43E−11 | 1.22E−07 | K(Ahx-palm)17, LERGG, R20 E24 E12 G2 |
| g723 | 8.95E−09 | 3.30E−10 | 7.61E−07 | K(gE-palm)17, LERGG, R20 E24 E12 G2 |
| g726 | 1.31E−08 | 7.91E−12 | 2.15E−07 | K(Ahx-palm)17, LERGG, R20 E24 E12 G2 E3 |
| g771 | 5.51E−12 | 1.75E−11 | 3.71E−08 | K(Ahx-palm)17, LERGG, R20 E24 E12 |
| g617 | no data | | | K(Ahx-palm)20, LERGG, G2, E12, |
| g787 | 4.36E−11 | 6.65E−09 | 0.00E+00 | K(Ahx-palm)20, LERGG, A24 E17 |
| g806 | 9.9E−12 | 1.71E−10 | 1.05E−07 | K(Ahx-palm)21, LERGG, A18 |
| g616 | no data | | | K(Ahx-palm)24, LERGG, G2, E12 |
| g701 | 3.83E−09 | 7.4E−09 | 0.00E+00 | K(gEpalm)12, LERGG, G2 E17 |

Parent sequence HSQGT5 FTSDY10 SKYLD15 SRRAQ20 DFVQW25 LVAGG extension Peptides in this section have the residues noted C-terminal to residue 30 and a C-terminal amide

| g316 | 1.06E−11 | 3.14E−11 | 3.65E−09 | SSGGSS |
| g317 | 0.00E+00 | 2.63E−09 | 0.00E+00 | SSGGSS K |
| g318 | 9.04E−09 | 1.14E−09 | 0.00E+00 | SSGGSSK(palm) |
| g402 | 5.96E−11 | 8.57E−11 | 0.00E+00 | SGSGSG |
| g319 | 1.04E−11 | 3.61E−11 | 0.00E+00 | PSSGA PPPSK |
| g320 | 3.20E−12 | 9.38E−12 | 1.01E−09 | PSSGA PPPSK(palm) |
| g315 | 5.04E−11 | 2.73E−11 | 1.97E−08 | GGGG |
| g325 | 1.03E−11 | 2.61E−11 | 0.00E+00 | GGGGK |
| g326 | 2.82E−12 | 2.47E−11 | 1.26E−08 | GGGGK(palm) |
| g327 | 2.32E−12 | 1.93E−11 | 1.28E−08 | GGGGK(gEpalm) |
| g321 | 2.79E−11 | 2.72E−11 | 6.41E−09 | KNNRNNIAK |
| g322 | 3.55E−12 | 1.06E−11 | 1.72E−09 | KNNRNNIAK(palm) |

Abbreviations:
K(gE-palm) = Lysine with a palmitoyl group conjugated to the epsilon nitrogen, through a gamma glutamic acid linker;
K (Ahx-palm) = Lysine with a palmitoyl group conjugated to the epsilon nitrogen, through an aminohexanoic acid linker;
K(bA-palm) = Lysine with a palmitoyl group conjugated to the epsilon nitrogen, through a beta alanine acid linker;
Aib, aminoisobutyric acid.
K(palm) = Lysine with a palmitoyl group directly conjugated to the epsilon nitrogen.

Glucagon and GLP-1 Receptor Mediated cAMP Production Assays in Presence of Plasma Concentrations of Serum Albumin (Assay 2).

Agonist potency determinations for peptides inducing cAMP production were measured in CHO cells expressing human, rat or mouse glucagon receptors (abbreviated to GlucR or GCGR) or GLP-1 receptors in the presence of human, rat or mouse serum albumin at 4.4, 3.2 and 3.2% respectively, as follows.

CHO cells with stable recombinant expression of the human, mouse or rat GlucR or GLP-1 receptor were cultured in DMEM 10% FBS and geneticin (100 pg/ml). Cryopreserved cells stocks were prepared in 1× cell freezing medium-DMSO serum free (Sigma Aldrich) at 2×10$^7$/vial and stored at −80° C. Cells were rapidly thawed at 37° C. and then diluted in to assay buffer (DMEM) containing serum albumin at 4.4, 3.2 and 3.2% for human, rat, and mouse serum albumin respectively. Peptides were serially diluted in DMSO and then diluted 100 fold into DMEM containing serum albumin at stated final concentration. Diluted peptides were then transferred into 384 black shallow well microtitre assay plates. Cells were added to the assay plates and incubated for 30 min at room temperature. Following incubation the assay was stopped and cAMP levels measured using the HTRF® dynamic d2 cAMP assay kit available from CisBio Bioassays, as per the manufacturers guidelines. Plates were read on Perkin Elmer ENVISION® fluorescence plate readers. Human and rat serum albumin were purchased from Sigma Aldrich and mouse serum albumin from Equitech Bio Ltd.

Data was transformed to % Delta F as described in manufacturer's guidelines and analysed by 4-parameter logistic fit to determine EC$_{50}$ values. Assay 2 EC$_{50}$ values for selected peptides are shown the Table 5. The assay 2 EC50 values determined are dependent on both the intrinsic potency of the peptides tested at the GLP1 and glucagon receptors in the recombinant cell lines and on the affinity of the peptide for serum albumin, which determines the amount of free peptide. Association with serum albumin increases the EC50 value obtained. The fraction of free peptide at plasma concentrations of albumin and the EC50 at 0% HSA can be calculated based on the variation in cAMP generation with the HSA concentration. For instance, G730 and G933 gave values of 0.85% and 0.29% for free peptide at 4.4% HSA and 7 pM and 6 pM for the EC50 at the GLP1R at 0% HSA respectively. G797 and G849 give values of 0.82% and 0.48% for free peptide at 4.4% HSA and 7 pM and 2 pM for the EC50 at the GLP1R at 0% HSA respectively. To compare the balance of activities at the GLP1R and GlucR between different peptides and across different conditions, these can be correlated using the calculation below, where the EC50's are related to those of the natural ligands.

The analysis was performed using a LC-system (LC Exigent LC) coupled to a medium high resolution mass

TABLE 5

EC50 Potencies for GLP-1/Glucagon Agonist Peptides in the Presence of Plasma Concentrations of Serum Albumin (Assay 2)

| Peptide | Assay in 4.4% Human Serum Albumin | | | Assay in 3.2% Mouse Serum Albumin | | | Assay in 3.2% Rat Serum Albumin | | |
|---|---|---|---|---|---|---|---|---|---|
| | Human GLP1R EC50 pM | Human GlucR EC50 pM | Human GlucR/ GLP1R Ratio[1] | Mouse GLP1R EC50 pM | Mouse GlucR EC50 pM | Mouse GlucR/ GLP1R Ratio[1] | Rat GLP1R EC50 pM | Rat GlucR EC50 pM | Rat GlucR/ GLP1R Ratio[1] |
| G730 | 455 | 402 | 0.122 | 1100 | 5460 | 0.04 | 81 | 45080 | 0.06 |
| G797 | 739 | 1137 | 0.07 | 290 | 764 | 0.08 | 60 | 23170 | 0.08 |
| G849 | 172 | 79 | 0.235 | 88 | 103 | 0.17 | 44 | 4055 | 0.33 |
| G933 | 943 | 564 | 0.179 | 540 | 377 | 0.29 | 136 | 15500 | 0.27 |
| G865 | 150 | 570 | 0.027 | 96 | 1100 | 0.021 | 18 | 87100 | 0.01 |
| G796 | 140 | 53 | 0.275 | 130 | 34 | 0.78 | 23 | 2000 | 0.36 |
| G812 | 316 | 764 | 0.044 | 130 | 947 | 0.032 | 19 | 14100 | 0.04 |
| G380 | 6543 | 53590 | 0.013 | 15000 | 576000 | 0.006 | | | |
| GLP1 | 25 | | | 21 | | | 1.9 | | |
| Glucagon | | 2.7 | | 9700 | 4.97 | | 557 | 60 | |

[1]GlucR/GLP1R ratios were determined as follows: Relative Potency GlucR = EC50 Glucagon/EC50 Tested peptide
Relative Potency GLP1R = EC50 GLP1/EC50 Tested peptide GlucR/GLP1R Ratio = Relative Potency GlucR/Relative Potency GLP1R Stability Testing of Peptides in Plasma.

The stability in plasma of the peptides G730, G797, G849 and G933 was determined as follows.

Stock solutions of the peptides of about 200 μmol/L was prepared by weighing solid peptide into a Eppendorf Low Bind Tube and dissolved in DMSO. 10 μL of stock solutions were added to 990 μL of plasma in an Eppendorf Low Bind Tube, resulting in initial concentrations of the peptides in plasma of about 2 μmol/L. The frozen blank plasma from human, rat and mouse had been thawed and heated to a temperature of 37° C. before addition of the stock solution. The spiked plasma samples were gently mixed and allowed to equilibrate for about 5 minutes before start of experiment. The plasma samples were incubated for 48 hours in a GalaxyR $CO_2$ incubator at 37° C. Sampling (30 μL) was performed at 0, 1, 2, 6.5, 17, 24 and 48 hours. The samples were stored at −70° C. until analysis.

spectrometer (Perkin Elmer PenTOF) with positive electrospray ionisation. The analytical column was a 5 cm, 1 mm Agilent Poroshell (custom made) C18-column with a particle size of 2.7 μm. Flow: 0.1 ml/min using a slow reversed phase gradient. Mobile phases used were acetonitrile and water containing 0.1% formic acid.

The resulting data were manually evaluated for the following degradation products: +1 product (acid) and the DPP IV-cleavage product. Products with +1 mass may arise from deamidation at amide groups of glutamine or at the C-terminus. Cleavage products arise from the action of the protease DPP IV in plasma. Both the degradation of the peptides and formation of peptide products were reported in percentage of the initial peptide concentration. Peaks were integrated and % remaining peptide was calculated: (peak area/peak area 0H)*100. Data for the 24 h time point is shown in Table 6. Levels of deamidation and DPP IV cleavage were low for G797 and G933.

TABLE 6

Peptide Stability in Plasma

| | Plasma Stability in Mouse Plasma at 24 h | | | Plasma Stability in Human Plasma at 24 h | | | Plasma Stability in Rat Plasma at 24 h | | |
|---|---|---|---|---|---|---|---|---|---|
| Peptide | % stable peptide | % +1 prod | % DPP cleaved product/+1 cleaved product | % stable peptide | % +1 prod | % DPP cleaved product/+1 cleaved product | % stable peptide | % +1 prod | % DPP cleaved product/+1 cleaved product |
| G730 | 65 | 15 | 14/5 | 100 | <1 | <1 | 24 | 58 | 2 |
| G797 | 84 | <1 | 1 | 85 | <1 | <1 | 60 | <1 | 1 |
| G849 | 38 | <1 | 22 | 100 | <1 | <1 | 69 | 16 | 3 |
| G933 | 83 | | 1 | 86 | | <1 | 85 | | <1 |

Plasma samples were assayed as follows. The 30 μL plasma samples were protein precipitated with 180 ml of cold ethanol in a 96-well low bind plate (Eppendorf Protein LoBind). After mixing and centrifugation 100 μl the supernatant was transferred to a new plate and 1 μl was injected onto an analytical column.

Solubility

Peptide solubility was assessed in a variety of buffer species within a pH range of 4.5 to 8.0, as follows. Dried powder forms of the GLP-1/Glucagon agonist peptides were reconstituted in various buffers at room temperature. The absorbance was measured at 280 nm using NanoDrop 2000 spectrophotometer and the peptide concentration was calculated using the following equation:

$$c = (A_{280} * M_w)/\varepsilon$$

where: c—concentration ε—extinction coefficient Mw—molecular weight $A_{280}$—Absorbance at 280 nm $$\varepsilon = (1 \times Trp = 5560) + (1 \times Tyr = 1200)$$

The Results are shown in Table 7. Each of the peptides was soluble at 0.8 mg/ml over a range of pH (6.5 to 8.5). G730 was soluble in a pH range 4.5 to 8.0, G797 was soluble in a pH range of 6. to 8.0, and G933 was soluble in a pH range of 6 to 8.0. The solubility of G933 was tested in a number of different buffer systems, also shown in Table 7. G933 was soluble at 1 mg/ml in at least the following buffer systems: histidine (pH 6 and 7; ionic strength:0.25 to 100 mM), sodium phosphate (pH 6-7.5; ionic strength:0.25 to 100 mM), and tris/hydroxymethyl aminomethane (pH 7-9; ionic strength:0.25 to 100 mM).

TABLE 7

Peptide solubility profile (Ionic Strength of all buffers: 100 mM)

| | Conc. (mg/ml) A280 Target 1 mg/ml | | | |
|---|---|---|---|---|
| Buffer | G730 | G797 | G849 | G933 |
| Glutamate pH 4.5 | 0.83 | 0.023 | NA | 0.02 |
| Acetate pH 5 | NA | NA | NA | 0.03 |
| Succinate pH 5 | NA | NA | NA | 1.1 |
| Phosphate, pH = 6 | 0.14 | 0.84 | 0.06 | 1.2 |
| Histidine pH 6 | NA | NA | NA | 1.2 |
| Phosphate pH 6.5 | 0.83 | 0.84 | NA | NA |
| Phosphate, pH 7.0 | NA | NA | NA | 1.1 |
| Histidine, pH 7.0 | NA | NA | NA | 1.1 |
| Phosphate pH 7.5 | 0.85 | 0.86 | NA | 1.2 |
| Tris pH 7.5 | 0.83 | 0.89 | 0.89 | 1.2 |
| Tris pH 8.0 | 1.1 | 0.83 | 0.89 | 1.2 |

Formulations.

Peptide solubility was assessed in three different isotonic formulations:
1. Default Formulation (DF)=0.1M Tris pH 7.5, 150 mM Mannitol. Final formulation pH=7.2
2. Back up formulation 1 (BF1)=0.05M Tris, 50 mM Arginine/Proline. Final formulation pH=8.0
3. Back up formulation 2 (BF2)=Sodium Phosphate buffer (pH8)/1.85% W/V propylene glycol. Final formulation pH=7.0

Solubility was measured as detailed above, and the results are shown in Table 8. G730, G797 and g933 were soluble to at least 5 mg/ml in the DF, the maximum solubility of G849 in DF was 3.7 mg/ml, G797 was soluble to at least 10 mg/ml in BF1, and G933 was soluble to at least 10 mg/ml in BF2.

TABLE 8

Peptide Solubility in Formulation

| Lead Candidate | Formulation Concentration | Formulation | 10 mg/ml solubility (BF2) |
|---|---|---|---|
| G730 | 5 mg/ml | DF | no |
| G797 | 5 mg/ml | DF/BF1 | yes |
| G849 | 3.7 mg/ml | DF | n/a |
| G933 | 5 mg/ml | DF | yes |

Concentration determined by A280 nm

The stability of the DF was evaluated by measuring purity reversed phase ultra-performance liquid chromatography (RP UPLC), within one month. The storage conditions were 5° C., 25° C., 40° C. and −80° C. The results are shown in Tables 9 and 10.

TABLE 9

Peptide formulation purity after 1 month in stability conditions

| Peptide | 5° C. | 25° C. | 40° C. | minus 80 C. |
|---|---|---|---|---|
| G730_DF | 97.7 | 96.1 | 86.1 | 97.7 |
| G797_BF1 | 98.72 | 98.84 | 77.54 | NA |
| G849_DF | 95.5 | NA | NA | NA |
| G933_DF | 97.8 | 95.9 | 88.9 | 98.9 |

TABLE 10

Peptide formulation purity loss (% compared to T0) after 1 month in stability conditions

| Lead Candidate | 5° C. | 25° C. | 40° C. | minus 80 C. |
|---|---|---|---|---|
| G730_DF | 0.82 | 2.43 | 12.54 | 0.3 |
| G797_BF1 | 0.24 | 0.12 | 21.65 | 0.3 |
| G849_DF | n/a | n/a | n/a | n/a |
| G933_DF | 0.3 | 2.2 | 9.3 | (−)0.8 |

The peptides all showed acceptable properties with respect to solubility, formulatability and stability Example 3: In Vivo Studies G730, G797, and G812 (Study A).

Selected GLP-1/glucagon agonist peptides disclosed herein were tested in a diet induced obesity (DIO) mouse model, as follows. Female C57/Bl6JHsdOla (obtained from Harlan Laboratories, UK) were started on a high fat diet of D12492 (Research Diets, NJ, USA) and a chocolate confection, delicato ball (Delicata Bakverk, Sweden) at 9-11 weeks of age, and were maintained on the diet for 16 weeks prior to arrival to the animal facility, during a three week acclimatizion period and during drug treatment, caloric content of the two components of the diet is shown in Table 11. The mice were divided into 9 groups (n=5-6), and treatment was started at 29 weeks of age. The treatment groups and dosing are shown in Table 12.

TABLE 11

Content of DIO Diet

| Product | Protein (%) | Carbohydrate (%) | Fat (%) | Kcal fat (%) | Total Kcal/gram |
|---|---|---|---|---|---|
| Delicatoball (Delicata Bakverk AB, Huddinge, Sweden) | 5 | 53 | 31 | 54 | 5.05 |
| D12492 (research Diets, NJ, USA) | 26.2 | 26.3 | 34.9 | 60 | 5.24 |

TABLE 12

Treatment Groups for Study A

| Peptide | Dose | # of Animals |
|---|---|---|
| Vehicle | NA | 6 |
| Liraglutide | 26.6 nmol/kg | 6 |
| G730 | 10 nmol/kg | 6 |
| G730 | 20 nmol/kg | 5 |
| G730 | 50 nmol/kg | 6 |
| G797 | 5 nmol/kg | 5 |
| G797 | 20 nmol/kg | 6 |
| G797 | 50 nmol/kg | 6 |
| G812 | 20 nmol/kg | 5 |

GLP-1/glucagon agonist peptides G730, G797, and G812, as well as Liraglutide were formulated in the vehicle, 100 mM Tris/150 mM mannitol, pH 7.4 The treatments were administered subcutaneously twice daily for 14 days, whilst the animals were maintained on a high fat diet. The body weight of the animals was monitored daily throughout the dosing period. At day 14, blood samples for the measurement of plasma glucose and insulin from conscious mice were obtained after a 4-hour fasting period. Mice were then anaesthetized using isoflourane and terminal blood was collected from the capillary bed behind the eye. The following parameters were measured: blood chemistry measurements of triglycerides, total cholesterol, non-esterified fatty acids (NEFA), beta-hydroxybutyrate and fibroblast growth factor 21 (FGF21) (Tables 14 and 15 below).

Figure 2:
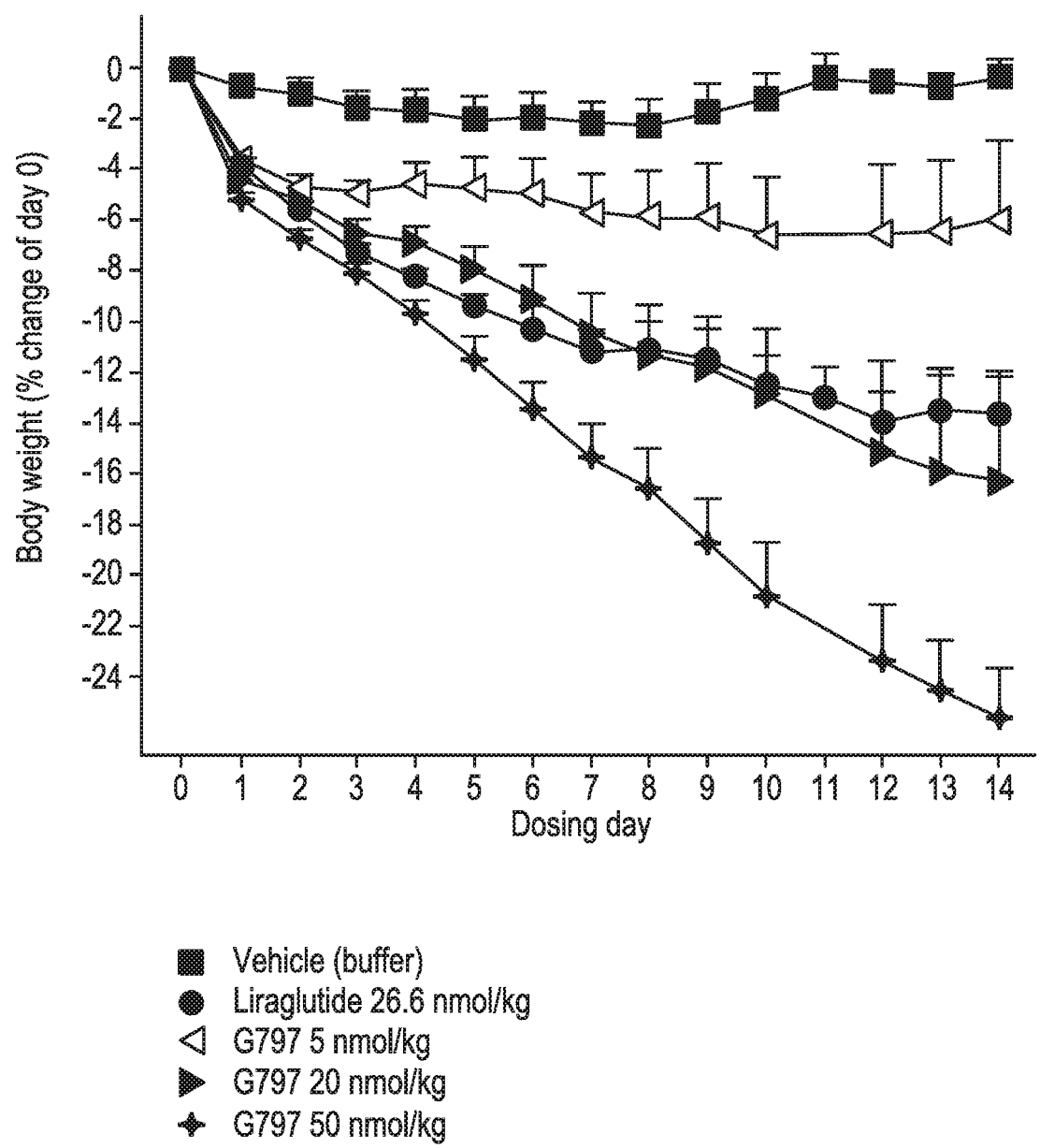
Figure 3:
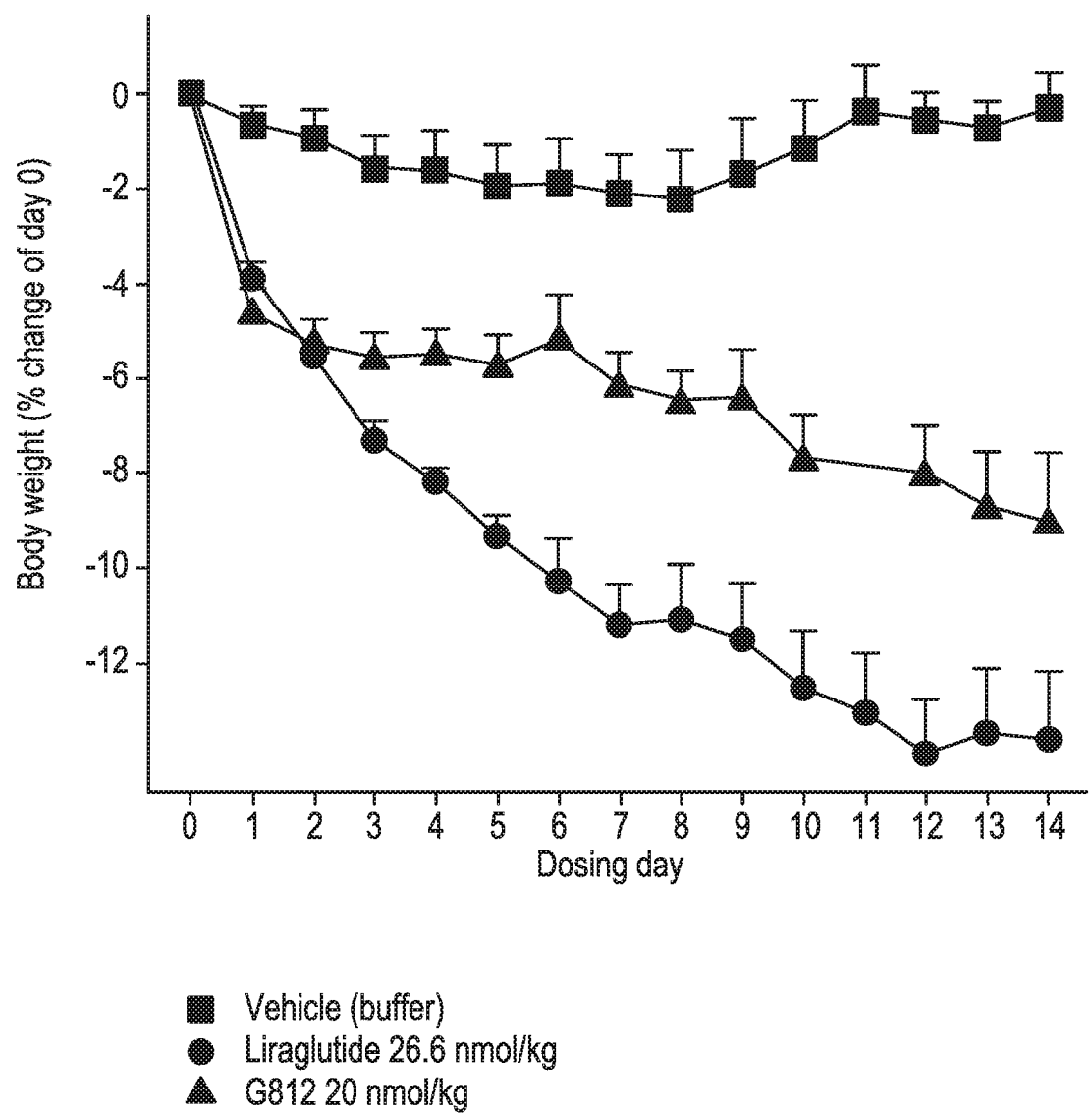
FIG. 3 shows the mean percent of change in body weight from day zero in DIO mice following administration of glucagon/GLP-1 co-agonist peptide G812 at a dose of 20 nmol/kg, compared to vehicle treatment, and treatment with Liraglutide. Starting body weight in the different groups were vehicle: 47.4±3.7 g and G812 20 nmol/kg: 49.2±3.4 g, respectively.
Figure 4:
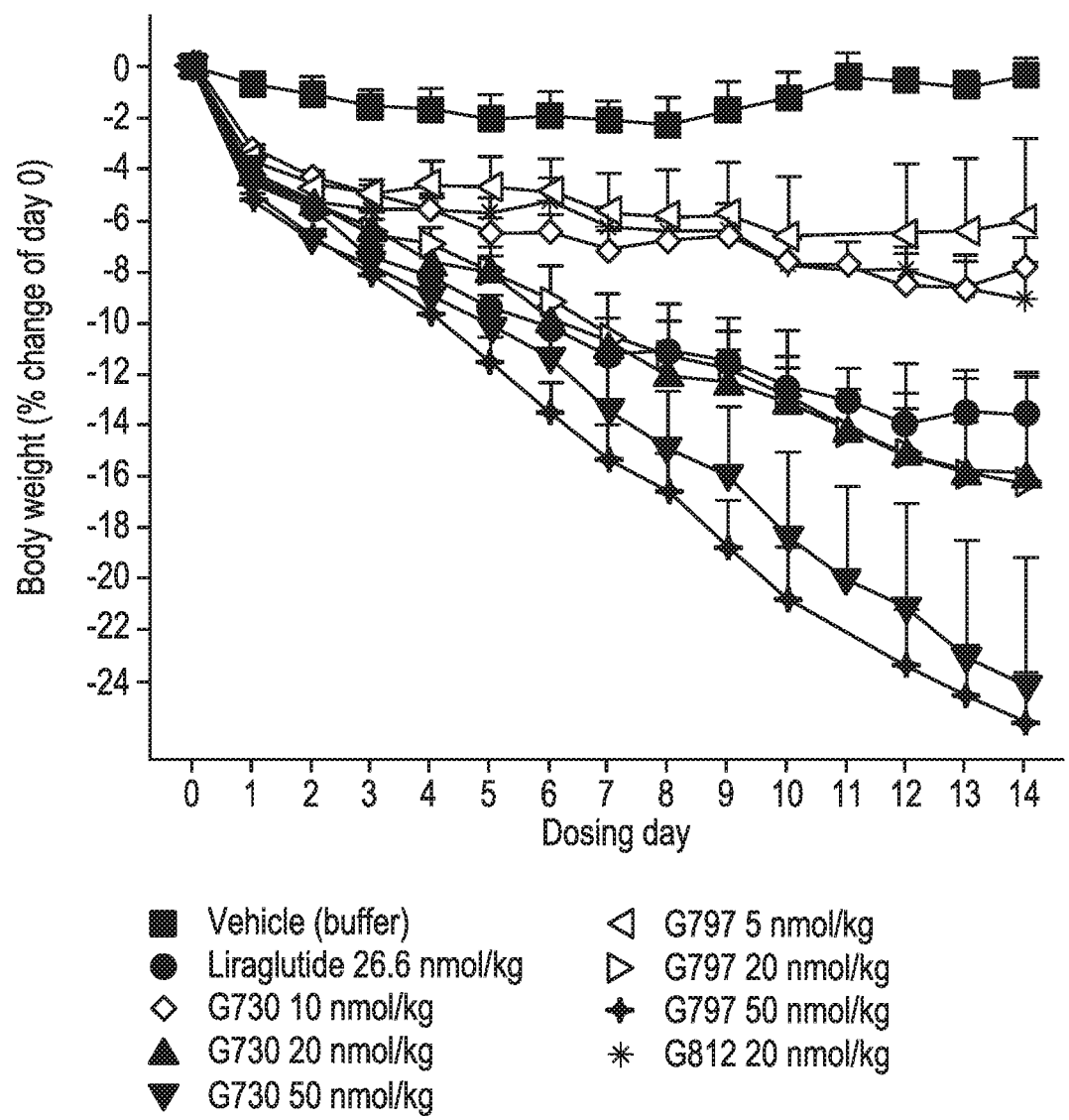
FIG. 4 is a graph comparing the change in body weight results for the three glucagon/GLP-1 co-agonist peptides presented in FIGS. 1, 2, and 3.

The effect of treatment with liraglutide and the GLP-1/glucagon agonist peptides G730, G797 and G812 on body weight, in comparison to liraglutide and vehicle, is shown in FIGS. 1-4. Animals treated with either G730 or G797 showed dose dependent and continuous weight loss over the 14 day dosing period. At 50 nmol/kg, animals treated with G730 and G797 experienced an about 24% change in weight at day 14 as compared to the vehicle-treated animals.

Mice treated with G730 or G797 showed a, dose-dependent reduction in glucose levels at day 14 (Table 13). Reduced insulin levels were also observed, with these two treatments, especially at the higher doses (Table 13). The insulin sensitivity index Homeostatic model assessment (HOMA) significantly improved at 20 nmol/kg G730 and 20 and 50 nmol/kg G797. HOMA is a modeling method that uses the sum of plasma insulin and glucose levels to assess β-cell function and insulin resistance (Table 14). Total plasma cholesterol was lowered both by liraglutide, G730 and G797 at all doses, with less pronounced changes in plasma non-esterified fatty acids (NEFA) levels and plasma and hepatic triglycerides (TG). Beta-hydroxybutyrate (BeHy) had tendencies towards increased levels, in line with the body weight loss. Fibroblast growth factor 21 (FGF21) generally increased with dual GLP-1/glucagon agonist peptide treatment.

TABLE 13

Effect of GLP-1/glucagon agonist peptide treatment on glucose, insulin, and HOMA

| Peptide | dose (nmol/kg) | start bw (g) | | SEM | BW day 14 (% change of vehicle mean) | | SEM | Glucose (mM) | | SEM | | Insulin (nM) | | SEM | | HOMA | | SEM | |
|---|---|---|---|---|---|---|---|---|---|---|---|---|---|---|---|---|---|---|---|
| vehicle | 0 | 47.4 | ± | 3.7 | 0.0 | ± | 0 | 8.8 | ± | 0.6 | | 0.8 | ± | 0.23 | | 7.2 | ± | 2.0 | |
| Liraglutide | 27 | 47.5 | ± | 1.8 | −13.3 | ± | 1.4 | 8.0 | ± | 0.2 | | 0.3 | ± | 0.12 | | 2.8 | ± | 1.1 | |
| G730 | 10 | 44.5 | ± | 2.2 | −7.5 | ± | 1.1 | 7.2 | ± | 0.3 | * | 0.4 | ± | 0.14 | | 3.3 | ± | 1.1 | |
| G730 | 20 | 45.9 | ± | 3.6 | −15.6 | ± | 2.2 | 6.7 | ± | 0.6 | * | 0.2 | ± | 0.06 | | 1.7 | ± | 0.5 | * |
| G730 | 50 | 46.1 | ± | 2.4 | −24.0 | ± | 5.1 | 5.9 | ± | 0.7 | * | 0.3 | ± | 0.13 | | 2.1 | ± | 1.0 | |
| G797 | 5 | 47.5 | ± | 1.2 | −5.7 | ± | 3.2 | 7.5 | ± | 0.3 | | 0.7 | ± | 0.25 | | 5.3 | ± | 2.0 | |
| G797 | 20 | 47.4 | ± | 2.2 | −16.0 | ± | 4.4 | 7.1 | ± | 0.6 | | 0.3 | ± | 0.09 | | 2.0 | ± | 0.8 | * |
| G797 | 50 | 47.2 | ± | 1.8 | −25.4 | ± | 2.0 | 6.6 | ± | 0.5 | * | 0.1 | ± | 0.01 | * | 0.6 | ± | 0.1 | * |
| G812 | 20 | 49.2 | ± | 3.4 | −8.7 | ± | 1.4 | 8.0 | ± | 0.4 | | 0.7 | ± | 0.23 | | 6.0 | ± | 2.1 | |

Results evaluated by a two-tailed distribution, two-sample unequal variance ttest;
*indicates p < 0.05 compared to vehicle.

TABLE 14

Effect of GLP-1/glucagon agonist peptide treatment on additional blood chemistry measurements

| Peptide | Dose (nmol/kg) | Hepatic TG (g TG/100 g Tissue) | | SEM | | Plasma TG (nM) | | SEM | | Plasma NEFA (nM) | | SEM |
|---|---|---|---|---|---|---|---|---|---|---|---|---|
| Vehicle | 0 | 13.6 | ± | 0.5 | | 0.19 | ± | 0.02 | | 0.22 | ± | 0.01 |
| Liraglutide | 27 | 13.1 | ± | 2.1 | | 0.24 | ± | 0.01 | | 0.24 | ± | 0.01 |
| G730 | 10 | 9.0 | ± | 0.9 | * | 0.21 | ± | 0.02 | | 0.28 | ± | 0.02 |
| G730 | 20 | 17.7 | ± | 3.4 | | 0.20 | ± | 0.03 | | 0.26 | ± | 0.03 |
| G730 | 50 | 28.1 | ± | 10.1 | | 0.23 | ± | 0.03 | | 0.32 | ± | 0.05 |
| G797 | 5 | 13.0 | ± | 1.1 | | 0.16 | ± | 0.02 | | 0.24 | ± | 0.03 |
| G797 | 20 | 17.7 | ± | 5.7 | | 0.14 | ± | 0.02 | | 0.27 | ± | 0.05 |
| G797 | 50 | 15.6 | ± | 5.8 | | 0.12 | ± | 0.02 | * | 0.24 | ± | 0.02 |
| G812 | 20 | 7.9 | ± | 0.6 | * | 0.13 | ± | 0.01 | * | 0.21 | ± | 0.01 |

| Peptide | Plasma Cholesterol (nM) | | SEM | | BeHy (umol/L) | | SEM | FGF21 (pg/mL) | | SEM |
|---|---|---|---|---|---|---|---|---|---|---|
| Vehicle | 4.65 | ± | 0.12 | | 389 | ± | 46 | 2757 | ± | 317 |
| Liraglutide | 3.75 | ± | 0.16 | * | 345 | ± | 21 | 2481 | ± | 650 |

TABLE 14-continued

Effect of GLP-1/glucagon agonist peptide treatment on additional blood chemistry measurements

| | | | | | | | | | | |
|---|---|---|---|---|---|---|---|---|---|---|
| G730 | * | 3.10 | ± | 0.16 | * | 428 | ± | 54 | 1963 | ± | 219 |
| G730 | | 2.45 | ± | 0.30 | * | 750 | ± | 318 | 2236 | ± | 300 |
| G730 | | 2.19 | ± | 0.23 | * | 1477 | ± | 479 | 5294 | ± | 2307 |
| G797 | | 3.32 | ± | 0.38 | * | 392 | ± | 111 | 2362 | ± | 342 |
| G797 | | 2.44 | ± | 0.27 | * | 659 | ± | 240 | 7277 | ± | 2455 |
| G797 | | 1.85 | ± | 0.07 | * | 1257 | ± | 285 | 5373 | ± | 813 | * |
| G812 | | 2.79 | ± | 0.24 | * | 333 | ± | 63 | 3207 | ± | 388 |

Results evaluated by a two-tailed distribution, two-sample unequal variance ttest;
* indicates $p < 0.05$ compared to vehicle.

G865, G933, and G796 (Study B).

A further set of GLP-1/glucagon peptides was tested in a diet induced obesity model using the same protocol above, but with the treatment groups and dosing shown in Table 15:

TABLE 15

Treatment Groups for Study B

| Peptide | Dose | # of Animals |
|---|---|---|
| Vehicle | NA | 6 |
| Liraglutide | 26.6 nmol/kg | 6 |
| G865 | 5 nmol/kg | 6 |
| G865 | 10 nmol/kg | 6 |
| G933 | 5 nmol/kg | 6 |
| G933 | 10 nmol/kg | 6 |
| G796 | 20 nmol/kg | 6 |
| G796 | 50 nmol/kg | 6 |

GLP-1/glucagon agonist peptides G865, G933, and G796, as well as liraglutide were formulated in the vehicle, 100 mM Tris/150 mM mannitol, pH 7.4 The treatments were administered subcutaneously twice daily for 14 days, whilst the animals were maintained on a high fat diet. The body weight of the animals was monitored daily throughout the dosing period At day 14, blood samples for the measurement of plasma glucose and insulin from conscious mice were obtained after a 4-hour fasting period. Mice were then anaesthetized using isoflourane and terminal blood was collected from the capillary bed behind the eye. The following parameters were measured: blood chemistry measurements of triglycerides, total cholesterol, non-esterified fatty acids (NEFA), beta-hydroxybutyrate and fibroblast growth factor 21 (FGF21) (Table 16 and Table 17 below).

Figure 5:
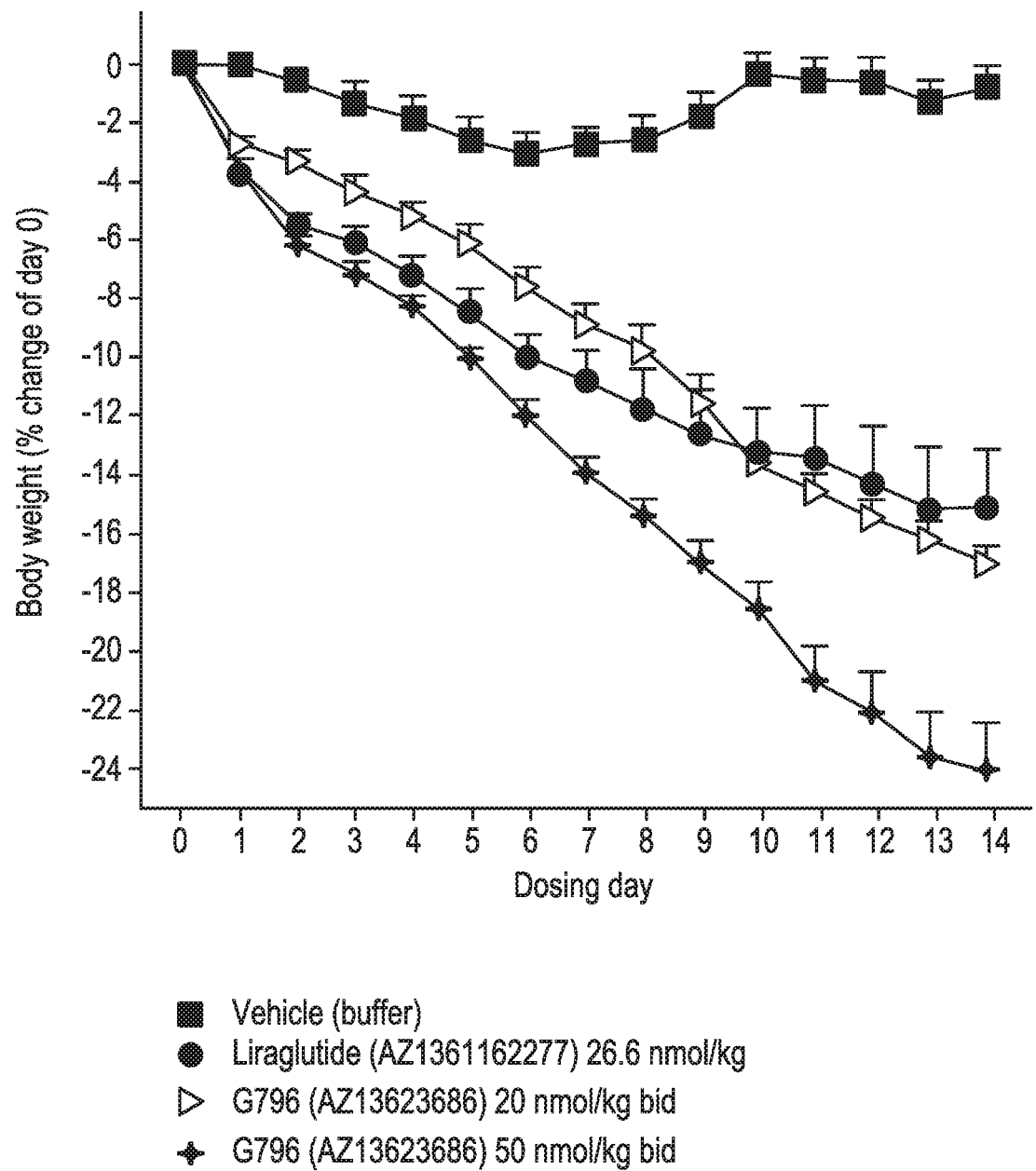
FIG. 5 shows the mean percent of change in body weight from day zero in DIO mice following administration of glucagon/GLP-1 co-agonist peptide G796 at two different doses, compared to vehicle treatment, and treatment with Liraglutide.
Figure 6:
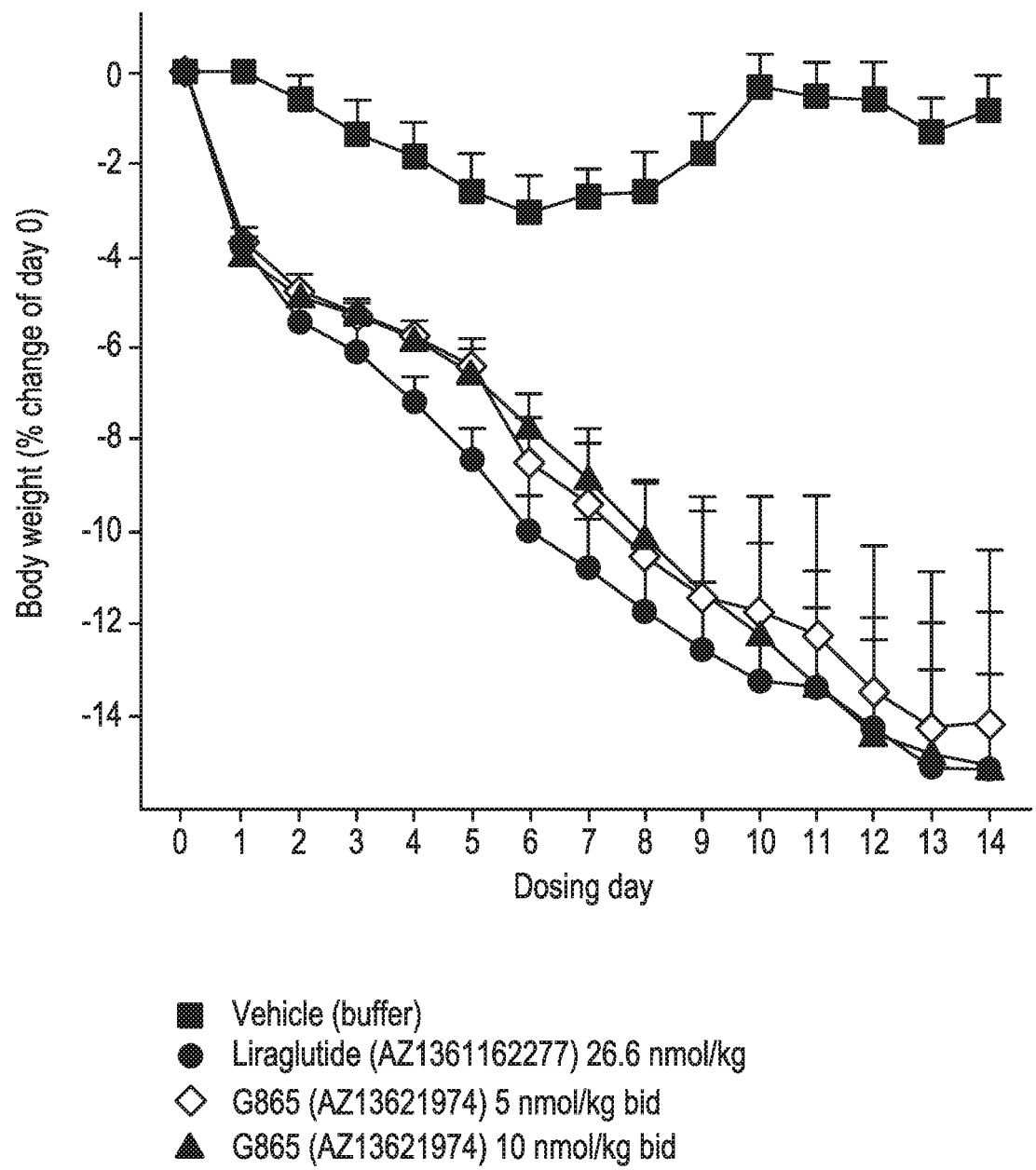
FIG. 6 shows the mean percent of change in body weight from day zero in DIO mice following administration of glucagon/GLP-1 co-agonist peptide G865 at two different doses, compared to vehicle treatment, and treatment with Liraglutide.
Figure 7:
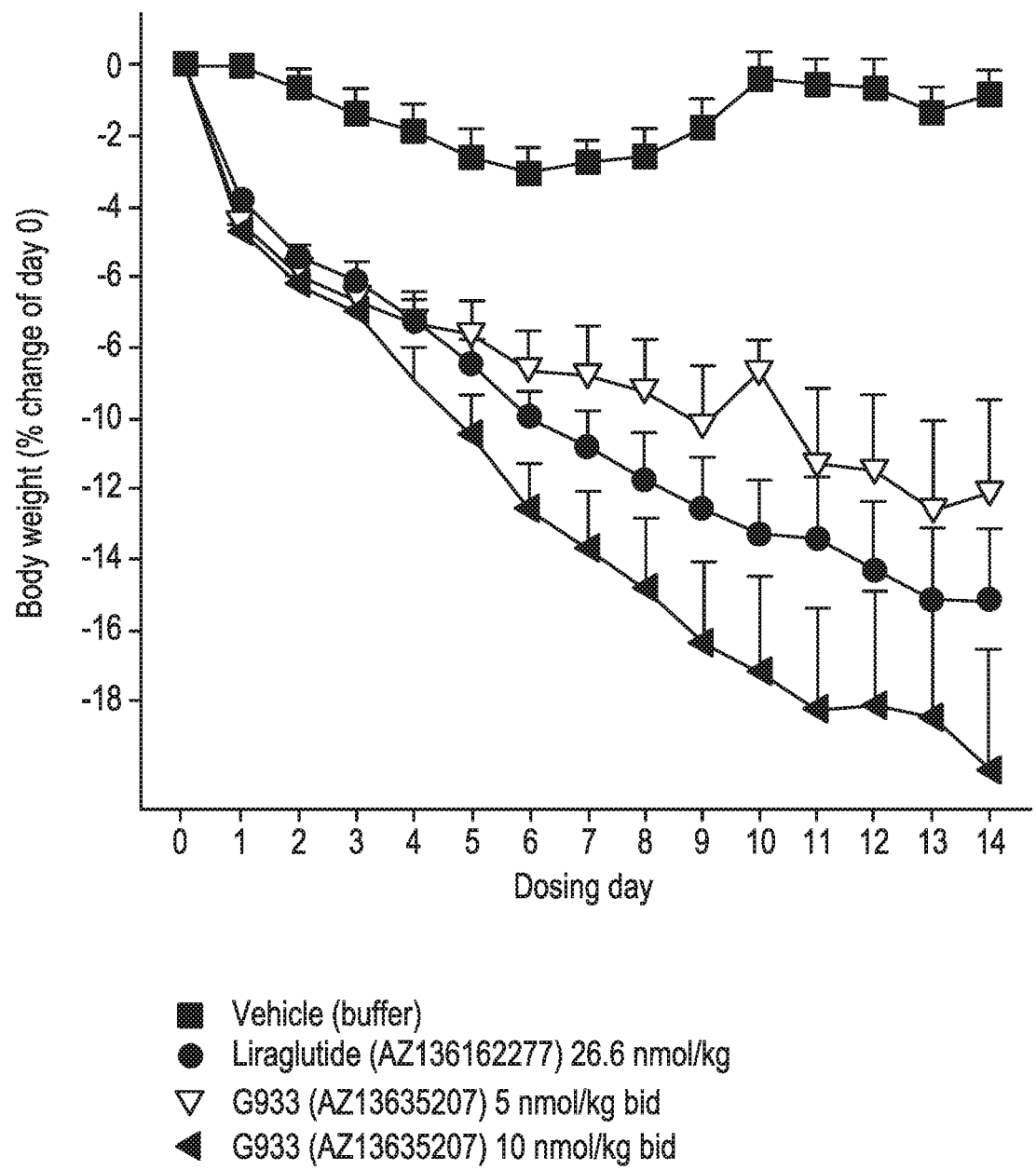
FIG. 7 shows the mean percent of change in body weight from day zero in DIO mice following administration of glucagon/GLP-1 co-agonist peptide G933 at two different doses, compared to vehicle treatment, and treatment with Liraglutide.
Figure 8:
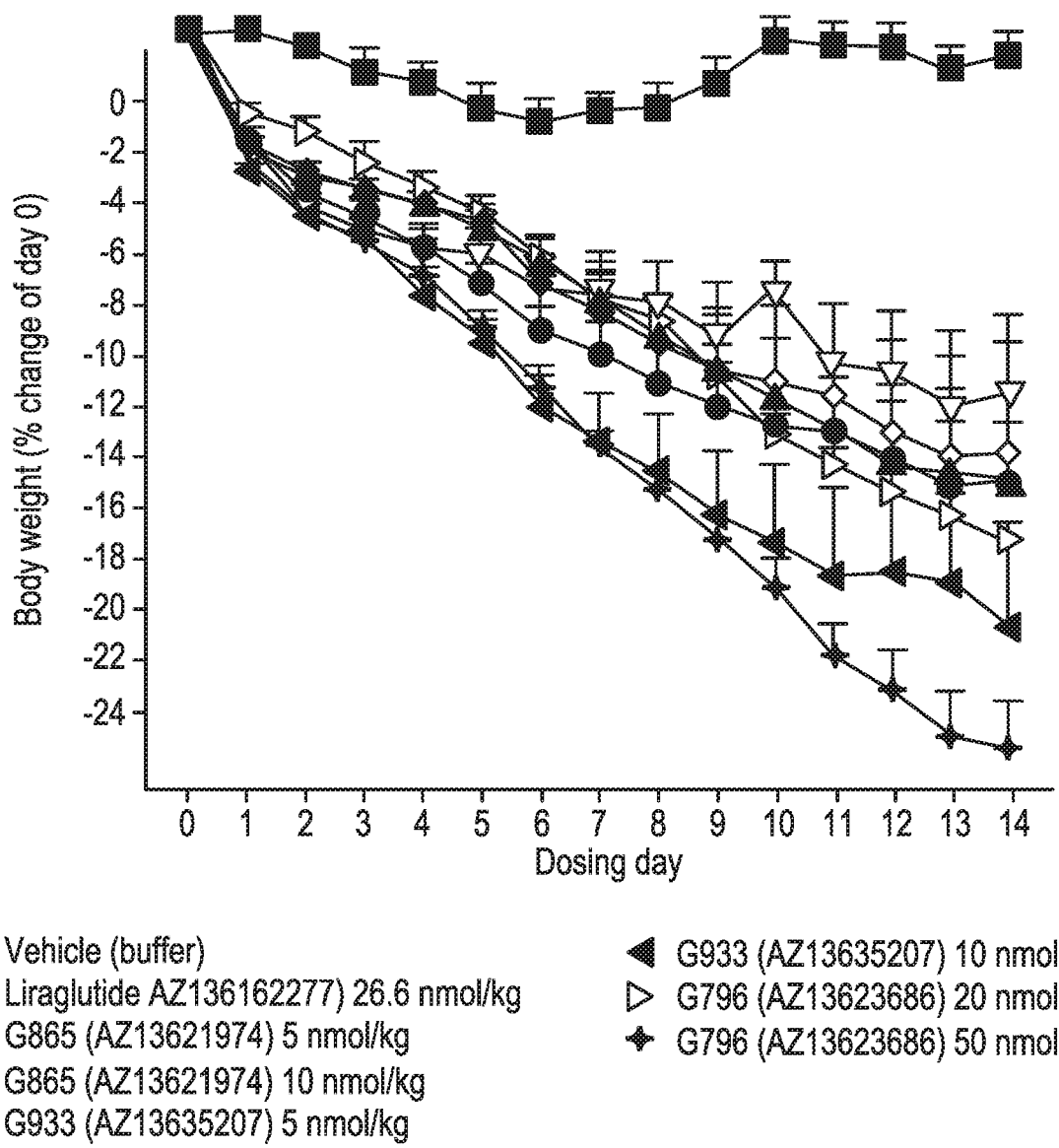
FIG. 8 is a graph comparing the change in body weight results for the three glucagon/GLP-1 co-agonist peptides presented in FIGS. 5, 6, and 7.

The effect of treatment with liraglutide and the GLP-1/glucagon agonist peptides G933, G865, G796 on body weight, in comparison to liraglutide and vehicle, is shown in FIGS. 5-8. Animals treated with either G933, G865 or G796 showed dose dependent and continuous weight loss over the 14 day dosing period.

Glucose levels, insulin levels and HOMA at day 14 post-treatment are shown in Table 16. Total plasma cholesterol levels, plasma non-esterified fatty acids (NEFA) levels, plasma and hepatic triglyceride (TG) levels, beta-hydroxy butyrate (BeHy) levels, and fibroblast growth factor 21 (FGF21) levels at day 14 post-treatment are shown in Table 17.

TABLE 16

Effect of GLP-1/glucagon agonist peptide treatment on glucose, insulin, and HOMA

| Peptide | dose (nmol/kg) | start bw (g) | | SEM | BW day 14 (% change of vehicle mean) | | SEM | Glucose (mM) | | SEM | Insulin (nM) | | SEM | | HOMA | | SEM | |
|---|---|---|---|---|---|---|---|---|---|---|---|---|---|---|---|---|---|---|
| vehicle | 0 | 46.9 | ± | 1 | 0 | ± | 0 | 8.7 | ± | 0.8 | 0.58 | ± | 0.09 | | 5.05 | ± | 0.8 | |
| Liraglutide | 27 | 46.3 | ± | 1.7 | −14 | ± | 2.1 | 7.7 | ± | 0.7 | 0.31 | ± | 0.07 | * | 2.51 | ± | 0.7 | * |
| G865 | 5 | 46.9 | ± | 0.8 | −4 | ± | 0.1 | 6.2 | ± | 0.6 * | 0.33 | ± | 0.08 | | 2.14 | ± | 0.6 | * |
| G865 | 10 | 47.0 | ± | 0.9 | −14 | ± | 3.4 | 6.6 | ± | 0.5 * | 0.36 | ± | 0.06 | | 2.43 | ± | 0.5 | * |
| G933 | 5 | 48.1 | ± | 1.6 | −11 | ± | 2.7 | 6.2 | ± | 0.8 | 0.53 | ± | 0.13 | | 3.31 | ± | 0.8 | |
| G933 | 10 | 48.6 | ± | 0.5 | −19 | ± | 3.5 | 7.2 | ± | 0.6 | 0.27 | ± | 0.07 | * | 1.98 | ± | 0.6 | * |
| G796 | 20 | 50.9 | ± | 1.3 | −16 | ± | 0.6 | 6.1 | ± | 0.2 * | 0.38 | ± | 0.05 | | 2.24 | ± | 0.2 | * |
| G796 | 50 | 49.7 | ± | 0.8 | −23 | ± | 1.6 | 6.4 | ± | 1.1 * | 0.43 | ± | 0.14 | | 2.87 | ± | 1.1 | |

Results evaluated by a two-tailed distribution, two-sample unequal variance ttest;
* indicates $p < 0.05$ compared to vehicle.

TABLE 17

Effect of GLP-1/glucagon agonist peptide treatment on additional blood chemistry measurements

| Peptide | dose (nmol/kg) | Hepatic TG (g TG/100 g tissue) | | SEM | Plasma TG (mM) | | SEM | | Plasma NEFA (mM) | |
|---|---|---|---|---|---|---|---|---|---|---|
| vehicle | 0 | 17.53 | ± | 1.30 | 0.25 | ± | 0.01 | | 0.28 | ± |
| Liraglutide | 27 | 18.4 | ± | 2.5 | 0.28 | ± | 0.03 | * | 0.29 | ± |
| G865 | 5 | 20.7 | ± | 5.6 | 0.26 | ± | 0.03 | | 0.29 | ± |
| G865 | 10 | 22.3 | ± | 5.1 | 0.23 | ± | 0.02 | | 0.27 | ± |

TABLE 17-continued

Effect of GLP-1/glucagon agonist peptide treatment on additional blood chemistry measurements

| | | | | | | | | | | | |
|---|---|---|---|---|---|---|---|---|---|---|---|
| G933 | 5 | 11.3 | ± | 0.8 | * | 0.19 | ± | 0.01 | * | 0.28 | ± |
| G933 | 10 | 14.7 | ± | 4.1 | | 0.16 | ± | 0.01 | * | 0.27 | ± |
| G796 | 20 | 9.6 | ± | 0.9 | * | 0.26 | ± | 0.05 | | 0.24 | ± |
| G796 | 50 | 9.9 | ± | 0.6 | * | 0.16 | ± | 0.01 | * | 0.21 | ± |

| Peptide | SEM | Plasma Cholesterol (mM) | | SEM | BeHy (umol/l) | | SEM | FGF21 (pg/mL) | | SEM |
|---|---|---|---|---|---|---|---|---|---|---|
| vehicle | 0.03 | 4.56 | ± | 0.33 | 387.52 | ± | 87.4 | 2002 | ± | 174 |
| Liraglutide | 0.02 | 3.26 | ± | 0.23 * | 572.25 | ± | 82.4 * | 2990 | ± | 729 |
| G865 | 0.05 | 3.06 | ± | 0.14 * | 775.06 | ± | 295.5 * | 8151 | ± | 4788 |
| G865 | 0.03 | 2.89 | ± | 0.24 * | 567.46 | ± | 169.3 * | 5953 | ± | 3409 |
| G933 | 0.03 | 2.88 | ± | 0.28 * | 673.08 | ± | 117.2 | 2682 | ± | 248 |
| G933 | 0.03 | 2.32 | ± | 0.20 * | 693.56 | ± | 158.3 * | 4459 | ± | 1249 |
| G796 | 0.02 * | 2.11 | ± | 0.07 * | 360.49 | ± | 51.1 | 6441 | ± | 1784 |
| G796 | 0.02 | 1.91 | ± | 0.05 * | 451.80 | ± | 63.4 | 9830 | ± | 3278 |

Results evaluated by a two-tailed distribution, two-sample unequal variance ttest;
* indicates p < 0.05 compared to vehicle.

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

---

What is claimed is:

1. A method of treating a disease or condition caused or characterized by excess body weight, comprising administering to a subject in need of treatment an effective amount of the peptide HSQGTFTSDKSEYLDSERARDFVAWLEAGG (SEQ ID NO: 19).

2. A method of reducing body weight in a subject comprising administering to a subject in need of treatment an effective amount of the peptide HSQGTFTSDKSEYLDSERARDFVAWLEAGG (SEQ ID NO: 19).

3. The method of claim 2, wherein attached to the lysine at position 10 of the peptide is a gammaE-palmitoyl.

* * * * *